United States Patent
Yonehara et al.

(10) Patent No.: US 9,812,509 B2
(45) Date of Patent: Nov. 7, 2017

(54) SENSOR

(71) Applicant: Kabushiki Kaisha Toshiba, Minato-ku (JP)

(72) Inventors: Toshiya Yonehara, Kawasaki (JP); Keiji Sugi, Fujisawa (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 15/156,953

(22) Filed: May 17, 2016

(65) Prior Publication Data
US 2016/0343775 A1 Nov. 24, 2016

(30) Foreign Application Priority Data

May 19, 2015 (JP) ................................. 2015-102008

(51) Int. Cl.
*H01L 29/08* (2006.01)
*H01L 27/28* (2006.01)
(Continued)

(52) U.S. Cl.
CPC ........ *H01L 27/288* (2013.01); *A61B 5/02427* (2013.01); *A61B 5/14552* (2013.01);
(Continued)

(58) Field of Classification Search
CPC .... A61B 2562/0233; A61B 2562/0247; A61B 2562/12; A61B 2562/16; A61B 2562/168;
(Continued)

(56) References Cited

U.S. PATENT DOCUMENTS 5,485,201 A * 1/1996 Aoki .................... G03B 7/16
348/223.1
6,491,647 B1 * 12/2002 Bridger .................. A61B 5/021
128/900
(Continued)

FOREIGN PATENT DOCUMENTS

JP 2012-115640 6/2012
JP 2013-150772 8/2013
(Continued)

OTHER PUBLICATIONS

Claire M. Lochner, et al., "All-organic optoelectronic sensor for pulse oximetry", Nature Communication, 2014, 12 pgs.
(Continued)

*Primary Examiner* — Mohammed Shamsuzzaman
(74) *Attorney, Agent, or Firm* — Oblon, McClelland, Maier & Neustadt, L.L.P.

(57) ABSTRACT

According to one embodiment, a sensor includes a light emitter and a light sensor. The light emitter includes a first electrode, a second electrode, and a first light emitting layer. The second electrode is light-transmissive. The first light emitting layer is provided between the first electrode and the second electrode. The light sensor includes a third electrode, a fourth electrode, a fifth electrode, a first photoelectric conversion layer, and a second photoelectric conversion layer. the fourth electrode is light-transmissive. The fifth electrode is provided between the third electrode and the fourth electrode. The fifth electrode is light-transmissive. The first photoelectric conversion layer is provided between the third electrode and the fifth electrode. The second photoelectric conversion layer is provided between the fourth electrode and the fifth electrode.

13 Claims, 26 Drawing Sheets

(51) Int. Cl.
  *H01L 51/50* (2006.01)
  *H01L 51/52* (2006.01)
  *A61B 5/024* (2006.01)
  *A61B 5/1455* (2006.01)
  *G01N 21/27* (2006.01)

(52) U.S. Cl.
  CPC ............ *G01N 21/27* (2013.01); *H01L 51/504* (2013.01); *H01L 51/5218* (2013.01); *H01L 51/5221* (2013.01); *A61B 2562/0233* (2013.01); *A61B 2562/12* (2013.01); *G01N 2201/0628* (2013.01)

(58) Field of Classification Search
  CPC .............. A61B 5/0215; A61B 5/02427; A61B 5/14552; G01N 21/27; G01N 2201/0628; H01L 27/288; H01L 51/504; H01L 51/5218; H01L 51/5221
  USPC ............ 257/40, 440; 1/1; 250/226, 206, 792
  See application file for complete search history.

(56) References Cited

U.S. PATENT DOCUMENTS

| | | | |
|---|---|---|---|
| 7,835,003 B2* | 11/2010 | Jiang | G01N 21/80 356/436 |
| 9,306,077 B2* | 4/2016 | Yamazaki | G02B 21/06 |
| 9,521,969 B2* | 12/2016 | Hirabara | A61B 5/0053 |
| 2004/0249252 A1* | 12/2004 | Fine | A61B 5/0059 600/322 |
| 2006/0241356 A1* | 10/2006 | Flaherty | A61B 5/04 600/301 |
| 2007/0210400 A1* | 9/2007 | Moribayashi | G02B 6/4214 257/440 |
| 2007/0281288 A1* | 12/2007 | Belkin | B01L 3/502715 435/4 |
| 2008/0202928 A1* | 8/2008 | Hyun | C12Q 1/001 204/403.01 |
| 2008/0249423 A1* | 10/2008 | Kitajima | A61B 5/02116 600/500 |
| 2008/0262321 A1* | 10/2008 | Erad | B01L 3/5027 600/301 |
| 2008/0317303 A1* | 12/2008 | Konno | G06K 9/2027 382/124 |
| 2009/0076322 A1* | 3/2009 | Matsunaga | A61B 1/041 600/109 |
| 2009/0205979 A1* | 8/2009 | Bekki | G01N 27/305 205/792 |
| 2009/0236496 A1* | 9/2009 | Tanada | G01J 1/44 250/206 |
| 2011/0178414 A1* | 7/2011 | Iijima | A61B 5/02427 600/479 |
| 2012/0071734 A1* | 3/2012 | Shimuta | A61B 5/0205 600/301 |
| 2012/0130211 A1 | 5/2012 | Kobayashi et al. | |
| 2013/0181120 A1* | 7/2013 | Shinto | G02B 5/0808 250/226 |
| 2014/0291480 A1* | 10/2014 | Bruder | G01C 3/06 250/206 |
| 2015/0280158 A1 | 10/2015 | Ogiwara et al. | |
| 2016/0015282 A1* | 1/2016 | Kim | A61B 5/02108 600/480 |
| 2016/0155391 A1* | 6/2016 | Takesue | G06F 3/1438 345/690 |
| 2016/0330389 A1* | 11/2016 | Adachi | H04N 5/357 |
| 2016/0341947 A1* | 11/2016 | Sato | G02B 21/06 |
| 2017/0042479 A1* | 2/2017 | Shimuta | A61B 5/0245 |
| 2017/0065177 A1* | 3/2017 | Sugi | A61B 5/0059 |
| 2017/0074652 A1* | 3/2017 | Send | G01C 3/08 |

FOREIGN PATENT DOCUMENTS

| | | |
|---|---|---|
| JP | 2014-75249 | 4/2014 |
| JP | 2014-150000 | 8/2014 |
| WO | WO 2016/166863 A1 | 10/2016 |
| WO | WO 2016/166864 A1 | 10/2016 |
| WO | WO 2016/166865 A1 | 10/2016 |

OTHER PUBLICATIONS

Ashu K. Bansal, et al., "Wearable Organic Optoelectronic Sensors for Medicine", Advance Materials, 2014, 16 pgs.

* cited by examiner

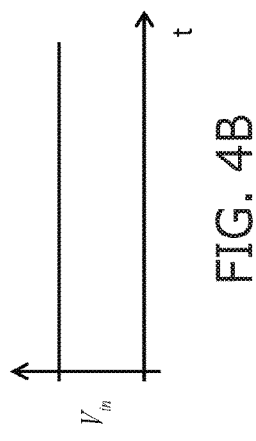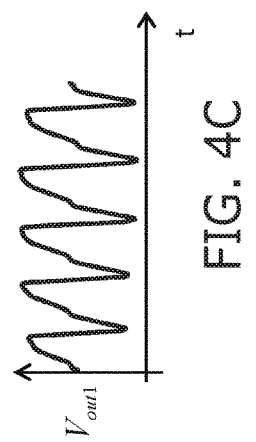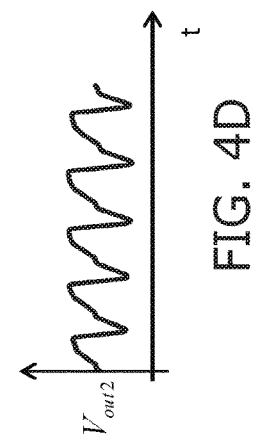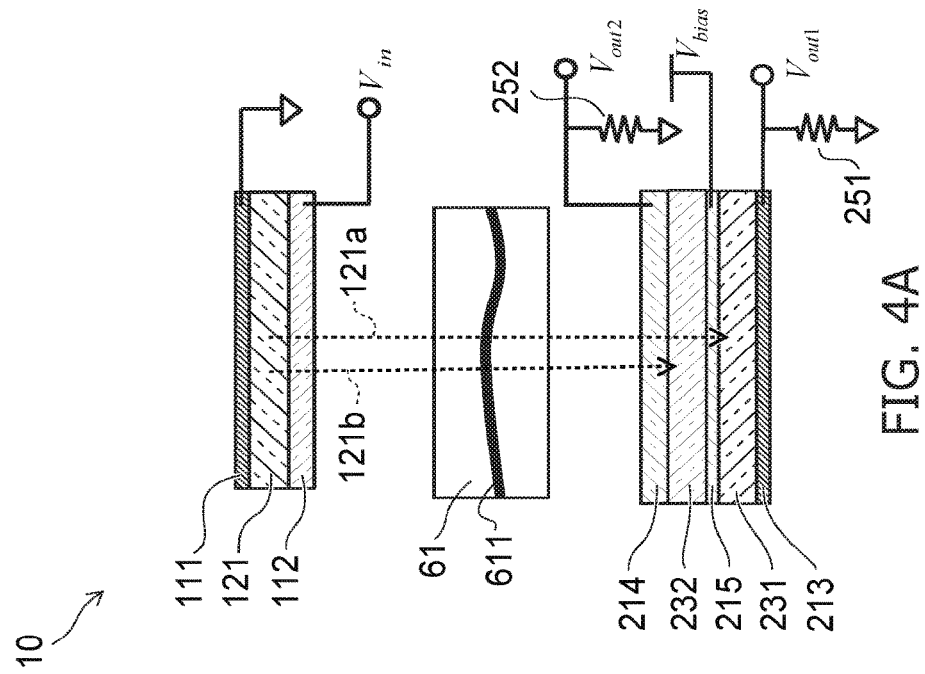

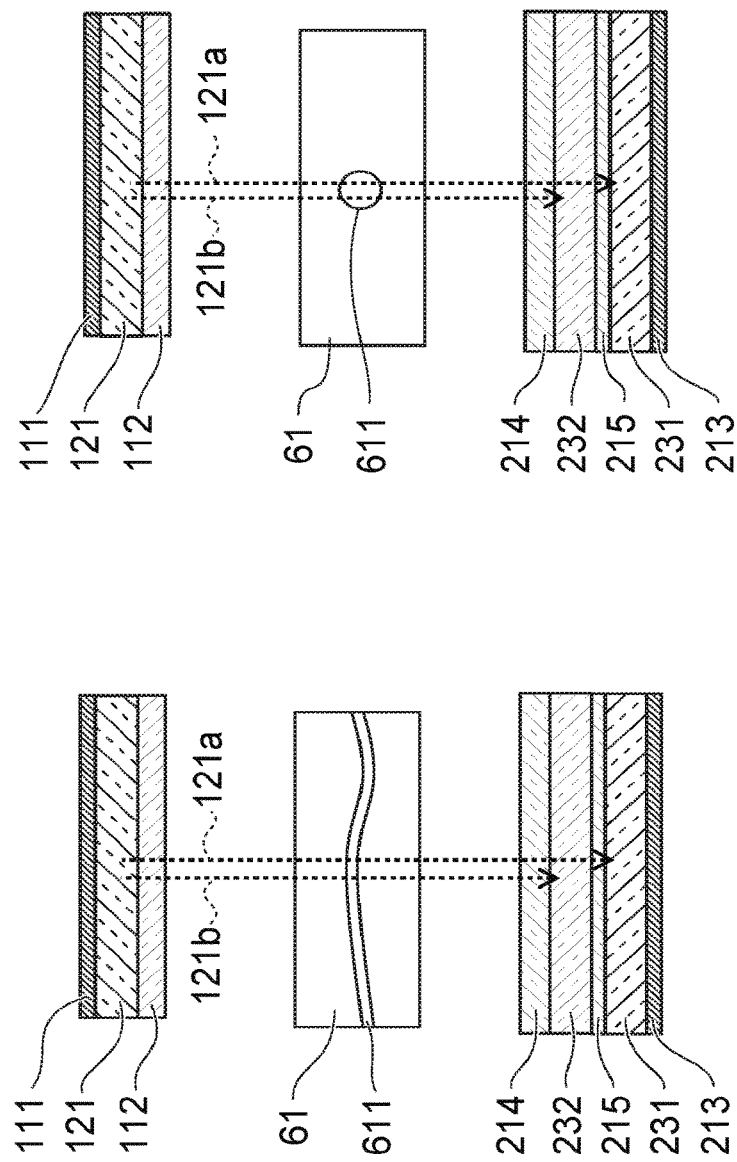

121  151

121  151  122

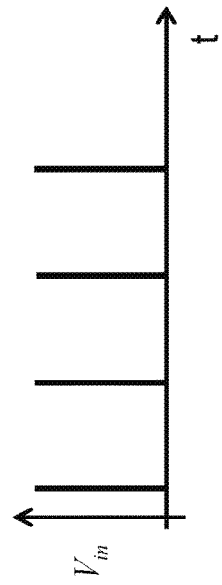
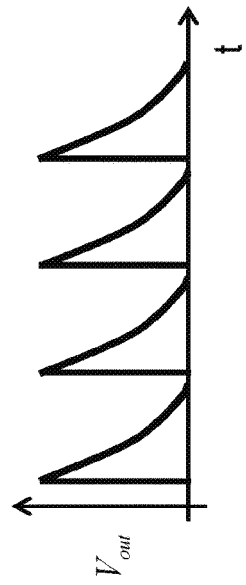
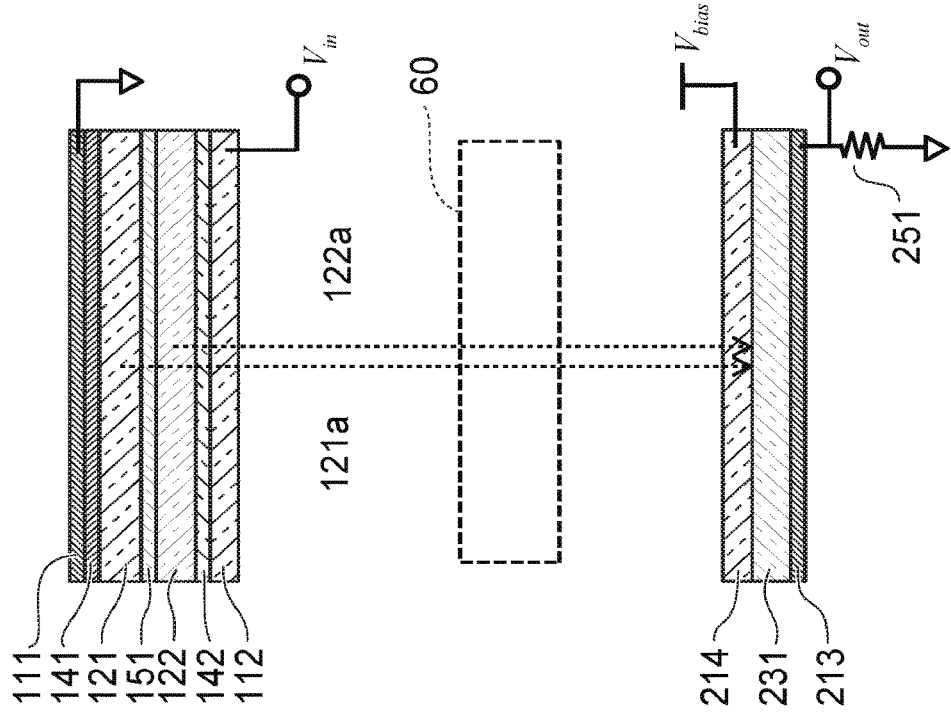

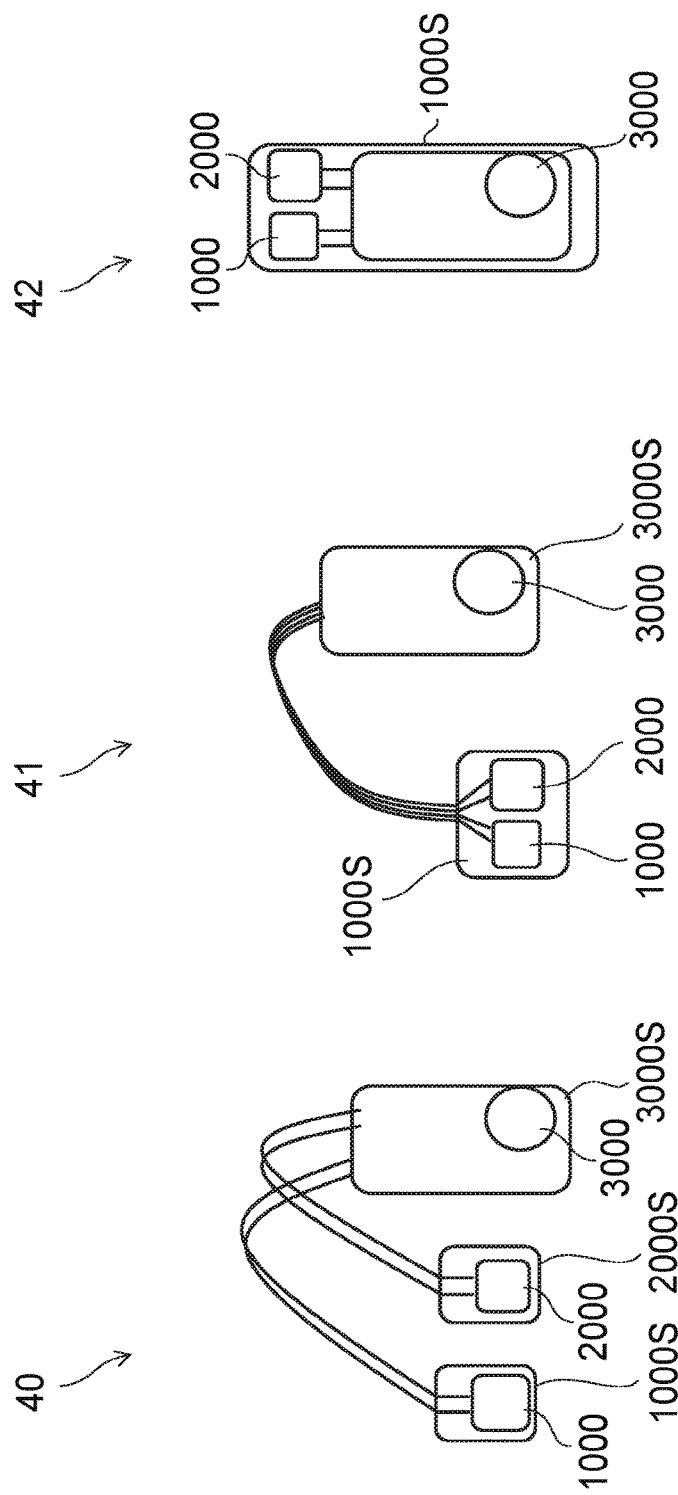

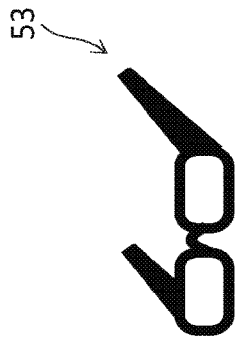
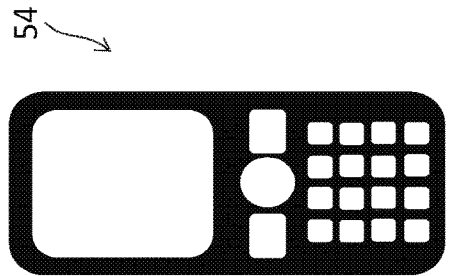
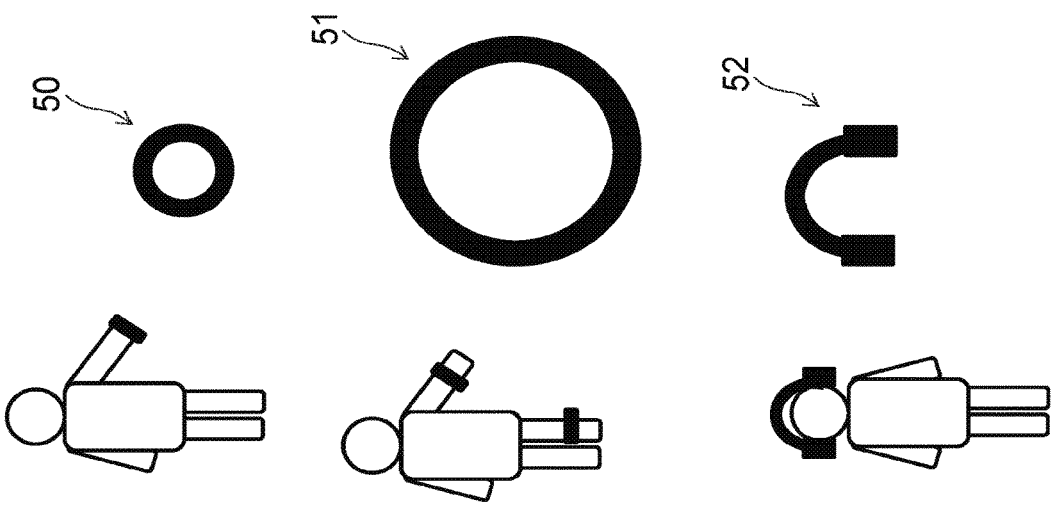
FIG. 25A  FIG. 25B  FIG. 25C  FIG. 25D  FIG. 25E

SENSOR

CROSS-REFERENCE TO RELATED APPLICATIONS

This application is based upon and claims the benefit of priority from Japanese Patent Application No. 2015-102008, filed on May 19, 2015; the entire contents of which are incorporated herein by reference.

FIELD

Embodiments described herein relate generally to a sensor.

BACKGROUND

There is a sensor that uses a light emitting element. For example, the sensor is used to sense a biological signal. The biological signal is sensed by light being radiated from the light emitting element and irradiated on an organism. It is desirable for the sensor to be small.

BRIEF DESCRIPTION OF THE DRAWINGS

FIG. 4A to FIG. 4D, FIG. 5A, and FIG. 5B are schematic views showing a method for measuring the blood oxygen concentration using the sensor according to the first embodiment;

FIG. 18A to FIG. 18C and FIG. 19A to FIG. 19C are schematic views showing the method for measuring the blood oxygen concentration using the sensor according to the third embodiment;

FIG. 24A to FIG. 24C are schematic views showing sensors according to the embodiment that are mounted;

FIG. 25A to FIG. 25E are schematic views showing applications of the sensor according to the embodiment.

DETAILED DESCRIPTION

Figure 1:
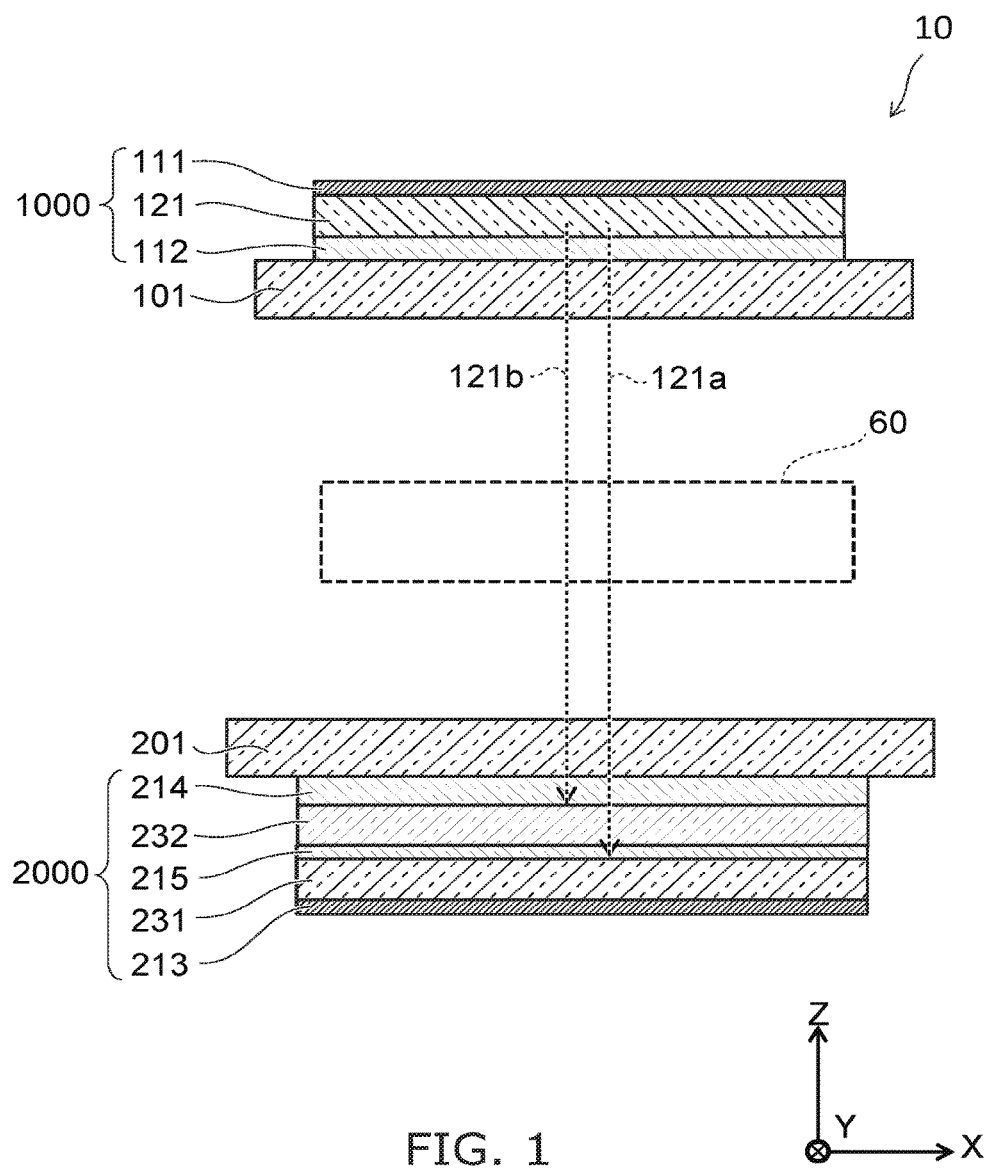
FIG. 1 is a schematic cross-sectional view showing an example of a sensor according to a first embodiment.

According to one embodiment, a sensor includes a light emitter and a light sensor. The light emitter includes a first electrode, a second electrode, and a first light emitting layer. The second electrode is light-transmissive. The first light emitting layer is provided between the first electrode and the second electrode. The light sensor includes a third electrode, a fourth electrode, a fifth electrode, a first photoelectric conversion layer, and a second photoelectric conversion layer. the fourth electrode is light-transmissive. The fifth electrode is provided between the third electrode and the fourth electrode. The fifth electrode is light-transmissive. The first photoelectric conversion layer is provided between the third electrode and the fifth electrode. The second photoelectric conversion layer is provided between the fourth electrode and the fifth electrode.

Embodiments of the invention will now be described with reference to the drawings.

The drawings are schematic or conceptual; and the relationships between the thicknesses and widths of portions, the proportions of sizes between portions, etc., are not necessarily the same as the actual values thereof. The dimensions and/or the proportions may be illustrated differently between the drawings, even in the case where the same portion is illustrated.

In the drawings and the specification of the application, components similar to those described therein above are marked with like reference numerals, and a detailed description is omitted as appropriate.

First Embodiment

FIG. 1 is a schematic cross-sectional view showing an example of a sensor according to a first embodiment.

As shown in FIG. 1, the sensor 10 includes a light emitter 1000 and a light sensor 2000. For example, the sensor 10 is used to sense a biological signal such as a pulse wave, a blood oxygen concentration, etc.

The light emitter 1000 includes a first electrode 111, a second electrode 112, and a first light emitting layer 121. The first light emitting layer 121 is provided between the first electrode 111 and the second electrode 112. For example, the light emitter 1000 is provided on a substrate 101.

A direction from the second electrode 112 toward the first electrode 111 is taken as a first direction. The first direction is, for example, a Z-direction shown in FIG. 1. Two directions perpendicular to each other and perpendicular to the first direction are taken as a second direction and a third direction. The second direction is, for example, an X-direction shown in FIG. 1. The third direction is, for example, a Y-direction shown in FIG. 1.

The light sensor 2000 includes a third electrode 213, a fourth electrode 214, a fifth electrode 215, a first photoelectric conversion layer 231, and a second photoelectric conversion layer 232. The fifth electrode 215 is provided between the third electrode 213 and the fourth electrode 214. The first photoelectric conversion layer 231 is provided between the third electrode 213 and the fifth electrode 215. The second photoelectric conversion layer 232 is provided between the fourth electrode 214 and the fifth electrode 215. For example, the light sensor 2000 is provided on a substrate 201.

In the sensor 10, at least a portion of the light emitter 1000 overlaps at least a portion of the light sensor 2000 in the first direction. A measurement object 60 is disposed between the light emitter 1000 and the light sensor 2000. At least a portion of the substrate 101 and at least a portion of the substrate 201 are provided between the light emitter 1000 and the light sensor 2000.

Light is radiated from the first light emitting layer 121 by injecting carriers into the first light emitting layer 121 from the first electrode 111 and the second electrode 112. The first light emitting layer 121 includes, for example, an organic substance. The first light emitting layer 121 may include an organic film that contains an organic substance.

The noise is smaller for the light radiated from a light emitting element including a light emitting layer including an organic substance than for the light radiated from a light emitting element including a light emitting layer including an inorganic compound. Therefore, the light that is radiated from the light emitting element including the light emitting layer including the organic substance is suited to applications that sense a measurement object outputting a faint signal such as a pulse wave, blood oxygen concentration, etc.

The light that is radiated from the first light emitting layer 121 is, for example, visible light. The light that is radiated from the light emitting layer 121 is, for example, one of red, orange, yellow, green, or blue light, or a combination of such light. The light that is radiated from the light emitting layer 121 may be ultraviolet light or infrared light. It is desirable for the spectral width of the light radiated from the first light emitting layer 121 to be as wide as possible. The full width at half maximum of the spectrum is, for example, 50 nm or more.

The material of the first photoelectric conversion layer 231 and the material of the second photoelectric conversion layer 232 are selected so that the wavelength of the light absorbed mainly by the first photoelectric conversion layer 231 is different from the wavelength of the light absorbed mainly by the second photoelectric conversion layer 232. Of the light radiated from the first light emitting layer 121, the first photoelectric conversion layer 231 selectively absorbs the light in the absorption wavelength region of the first photoelectric conversion layer 231. Of the light radiated from the first light emitting layer 121, the second photoelectric conversion layer 232 selectively absorbs the light in the absorption wavelength region of the second photoelectric conversion layer 232.

The difference between the wavelength of the light selectively absorbed by the first photoelectric conversion layer 231 and the wavelength of the light selectively absorbed by the second photoelectric conversion layer 232 is, for example, 50 nm or more. In other words, the difference between the absorption peak wavelength of the first photoelectric conversion layer 231 and the absorption peak wavelength of the second photoelectric conversion layer 232 is, for example, 50 nm or more. It is more desirable for the difference to be 100 nm or more. Here, the absorption peak wavelength means the wavelength having the maximum absorbance of the absorption spectra of each photoelectric conversion layer.

For example, the light that is radiated from the first light emitting layer 121 may include multiple peak wavelengths. As an example of such a case, light 121a and light 121b are radiated from the first light emitting layer 121. The light 121a has a first peak wavelength. The light 121b has a second peak wavelength that is different from the first peak wavelength. The intensity of the light 121a has a maximum at the first peak wavelength. The intensity of the light 121b has a maximum at the second peak wavelength. The difference between the first peak wavelength and the second peak wavelength is, for example, 50 nm or more. The material of the first light emitting layer 121 is selected so that the first peak wavelength and the second peak wavelength are included in a wavelength region where the light sensor 2000 has sensing sensitivity.

The light 121a and the light 121b pass through the measurement object 60 and are incident on the first photoelectric conversion layer 231 and the second photoelectric conversion layer 232. When the light is incident on the first photoelectric conversion layer 231 and the second photoelectric conversion layer 232, carriers are generated in each of the photoelectric conversion layers. Thereby, a current that corresponds to the amount of the carriers generated in the first photoelectric conversion layer 231 flows between the third electrode 213 and the fifth electrode 215. A current that corresponds to the amount of the carriers generated in the second photoelectric conversion layer 232 flows between the fourth electrode 214 and the fifth electrode 215. The state of the measurement object 60 is sensed by sensing these currents. For example, the measurement is performed using the light having multiple peak wavelengths as shown in FIG. 1.

The first photoelectric conversion layer 231 and the second photoelectric conversion layer 232 include organic substances. The first photoelectric conversion layer 231 and the second photoelectric conversion layer 232 may include organic films that contain organic substances. The organic substance that is included in the second photoelectric conversion layer 232 may be different from the organic substance included in the first photoelectric conversion layer 231. The wavelength of the light absorbed mainly by the second photoelectric conversion layer 232 is different from the wavelength of the light absorbed mainly by the first photoelectric conversion layer 231. In the case where the first light emitting layer 121 radiates the light 121a and the light 121b having mutually-different peak wavelengths, for example, the peak wavelength region of the light 121a is absorbed mainly by the first photoelectric conversion layer 231; and the peak wavelength region of the light 121b is absorbed mainly by the second photoelectric conversion layer 232.

The substrate 101, the substrate 201, the second electrode 112, the fourth electrode 214, the fifth electrode 215, and the second photoelectric conversion layer 232 are light-transmissive. The reflectance of the first electrode 111 is higher than the reflectance of the second electrode 112. For example, the first electrode 111 is light-reflective and reflects the light radiated from the first light emitting layer 121 toward the second electrode 112.

Figure 2:
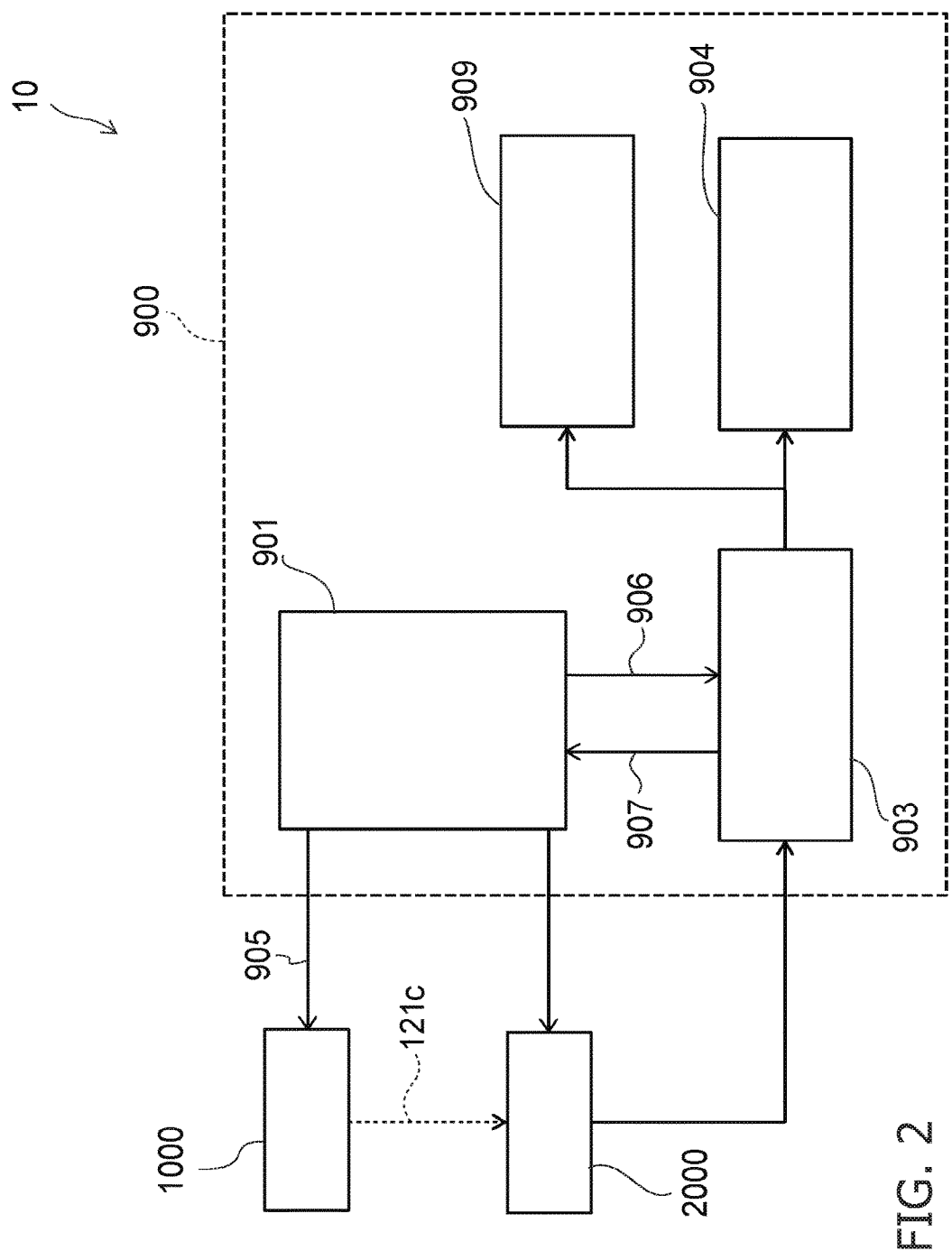
FIG. 2 and FIG. 3 are schematic views showing an example of the sensor according to the first embodiment.
Figure 3:
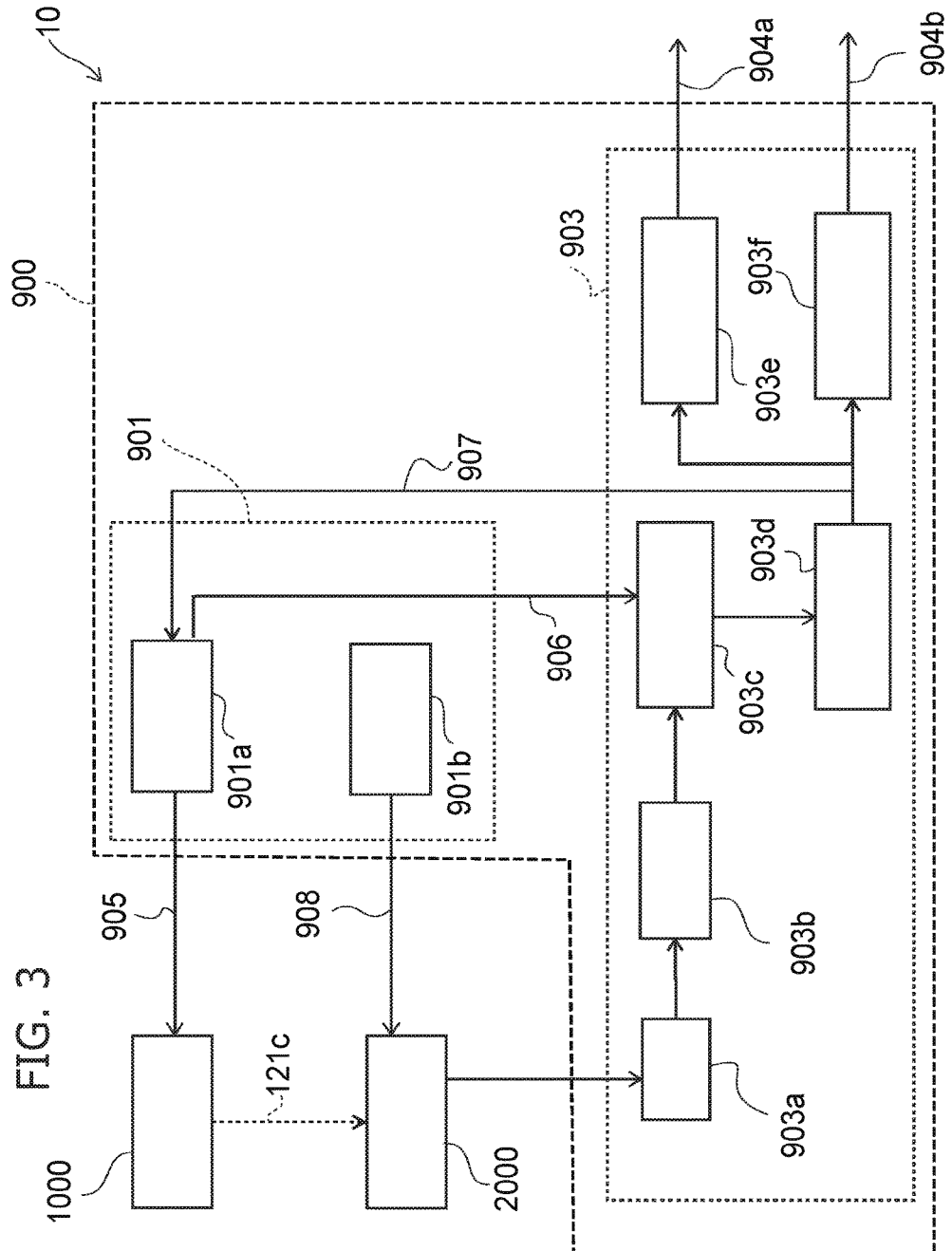

FIG. 2 and FIG. 3 are schematic views showing an example of the sensor according to the first embodiment.

As shown in FIG. 2, the sensor 10 may include a processor 900 in addition to the light emitter 1000 and the light sensor 2000. The processor 900 includes, for example, a controller 901, a signal processor 903, a recording device 904, and a display device 909.

When a signal is transmitted from the controller 901 to the light emitter 1000, light 121c is radiated from the light emitter 1000. The light 121c includes, for example, the light 121a having the first peak wavelength and the light 121b having the second peak wavelength shown in FIG. 1. The light 121c passes through the not-shown measurement object and is incident on the light sensor 2000. A bias signal may be transmitted from the controller 901 to the light sensor 2000 to increase the sensitivity of the light sensor 2000.

The signal that is sensed by the light sensor 2000 is output to the signal processor 903. For example, the signal processor 903 performs appropriate processing of the signal that is input such as AC detection, signal amplification, noise removal, etc. Subsequently, the signal processor 903 performs analysis of the pulse wave and/or blood oxygen concentration of the measurement object based on the signal output from the light sensor 2000. The signal processor 903 may receive a synchronization signal from the controller 901 to perform the appropriate signal processing. A feedback signal for adjusting the light amount of the light emitter 1000 may be transmitted to the controller 901 from the signal processor 903. The signal that is generated by the signal processor 903 is stored in the recording device 904; and the information is displayed in the display device 909.

The processor 900 may not include the recording device 904 and the display device 909. In such a case, for example, the signal that is generated by the signal processor 903 is output to a recording device and a display device outside the sensor 10.

The sensor 10 that includes the processor 900 will now be described in detail with reference to FIG. 3. As shown in FIG. 3, the light emitter 1000 receives an input signal 905 including a DC bias signal or a pulse signal from a pulse generator 901a of the controller 901. The light 121c that is radiated from the light emitter 1000 passes through the measurement object and is sensed by the light sensor 2000. The light sensor 2000 may receive a bias signal from a bias circuit 901b of the controller 901.

The signal that is sensed by the light sensor 2000 is input to the signal processor 903. In the signal processor 903, after the signal that is output from the light sensor 2000 is subjected to AC detection as necessary, the signal is amplified by an amplifier 903a and subjected to the removal of unnecessary noise components by a filter unit 903b. The signal that is output from the light sensor 2000 may be subjected to the removal of the noise components by the filter unit 903b and then amplified by the amplifier 903a after the signal is subjected to the AC detection as necessary.

A signal synchronizer 903c receives the signal output from the filter unit 903b, receives a synchronization signal 906 from the controller 901 as appropriate, and synchronizes with the light 121c. The signal that is output from the signal synchronizer 903c is input to a signal shaper 903d. The processor 900 may not include the signal synchronizer 903c. In such a case, the signal that is output from the filter unit 903b is input to the signal shaper 903d without the signal synchronizer 903c being interposed.

The signal shaper 903d shapes the signal into the desired signal to perform the appropriate signal processing by a signal calculator 903e. For example, time averaging or the like is performed as the signal shaping. In the signal processor 903, the order of the AC detection and the processing performed by the processors is modifiable as appropriate.

The signal that is processed by the signal shaper 903d is output to the signal calculator 903e and a saturated oxygen concentration calculator 903f. In the signal calculator 903e, for example, the calculation of the pulse is performed; and a pulse value 904a is output to the recording device and the display device. In the saturated oxygen concentration calculator 903f, the calculation of the saturated oxygen concentration in the blood is performed; and a saturated oxygen concentration value 904b is output to the recording device and the display device.

FIG. 4A to FIG. 4D, FIG. 5A, and FIG. 5B are schematic views showing a method for measuring the blood oxygen concentration using the sensor according to the first embodiment. The substrate 101 and the substrate 201 are not shown in FIG. 4A. FIG. 4A shows the state when the oxygen concentration inside a blood vessel 611 of a finger 61 is measured using the sensor 10. Other than a finger, the oxygen concentration of the blood can be measured using the sensor 10 also at an ear, the chest, an arm, etc.

In FIG. 4B to FIG. 4D, the horizontal axis is the time t. The vertical axis of FIG. 4B is an input signal $V_{in}$ input between the first electrode 111 and the second electrode 112 of the light emitter 1000. The vertical axis of FIG. 4C is a first output signal $V_{out1}$ sensed by the first photoelectric conversion layer 231. The vertical axis of FIG. 4D is a second output signal $V_{out2}$ sensed by the second photoelectric conversion layer 232.

As shown in FIG. 4B, for example, a constant voltage is applied as the input signal $V_{in}$ between the first electrode 111 and the second electrode 112 of the light emitter 1000. The light is radiated from the first light emitting layer 121 according to the voltage applied between the first electrode 111 and the second electrode 112.

In the example shown in FIG. 4A, the light 121a and the light 121b are radiated from the light emitter 1000. The light 121a and the light 121b pass through the blood vessel 611 and are sensed by the light sensor 2000. Specifically, the light 121a is absorbed by the first photoelectric conversion layer 231; and the light 121b is absorbed by the second photoelectric conversion layer 232.

When the light 121a is absorbed by the first photoelectric conversion layer 231, electrons and holes which are carriers are generated in the interior of the first photoelectric conversion layer 231. The electrons and the holes travel oppositely from each other toward the third electrode 213 or the fifth electrode 215. Thereby, a current flows in the circuit connected to the third electrode 213 and the fifth electrode 215. The flow of the current is converted to a voltage by a resistor 251. The voltage is output as the first output signal $V_{out1}$.

Similarly, when the light 121b is absorbed by the second photoelectric conversion layer 232, electrons and holes are generated in the interior of the second photoelectric conversion layer 232. The electrons and the holes travel oppositely from each other toward the fourth electrode 214 or the fifth electrode 215. Thereby, a current flows in the circuit connected to the fourth electrode 214 and the fifth electrode 215. The flow of the current is converted into a voltage by a resistor 252. The voltage is output as the second output signal $V_{out2}$.

At this time, as shown in FIG. 4C and FIG. 4D, the signal in the blood is superimposed onto the first output signal $V_{out1}$ and the second output signal $V_{out2}$. The pulse is obtained by measuring the time interval of each pulse included in the output signal of FIG. 4C or FIG. 4D.

A blood oxygen concentration S is expressed by the following Formula (1).

$$S = \frac{C2}{C1 + C2} \quad (1)$$

C1 is the concentration of hemoglobin (deoxyhemoglobin) not bonded to oxygen in the blood. C2 is the concentration of hemoglobin (oxyhemoglobin) bonded to oxygen in the blood.

Formula (1) can be expressed by the following Formula (2), where C1/C2 is R.

$$S = \frac{1}{1+R} \quad (2)$$

It can be seen from Formula (2) that the blood oxygen concentration can be obtained if the ratio of C1 and C2 is known.

A transmittance T1 of the systole of the blood vessel is expressed by the following Formula (3). A transmittance T2 of the diastole of the blood vessel is expressed by the following Formula (4).

$$T1 = I_o \exp[-kd] \exp[-(E1C1+E2C2)d1] \quad (3)$$

$$T2 = I_o \exp[-kd] \exp[-(E1C1+E2C2)d2] \quad (4)$$

$I_o$ is the incident intensity. k is an absorption coefficient other than that of the blood vessel. d is the optical path length other than that of the blood vessel. d is a constant. E1 is the molar absorbance of deoxyhemoglobin. E2 is the molar absorbance of oxyhemoglobin. d1 is the optical path length of the light of the systole of the blood vessel. d2 is the optical path length of the light of the diastole of the blood vessel.

The following Formula (5) is obtained by dividing the sides of Formula (3) respectively by the sides of Formula (4) and by calculating the natural logarithm of both sides.

$$\ln \frac{T1}{T2} = -(E1R + E2)A, \quad A = C2(d1-d2) \quad (5)$$

In Formula (5), there are two unknown values, i.e., R and A, because E1 and E2 at each wavelength are known. Accordingly, A can be eliminated and the value of R can be obtained by determining $\ln(T1(\lambda_1)/T2(\lambda_1))$ and $\ln(T1(\lambda_2)/T2(\lambda_2))$ using two types of lights having mutually-different wavelengths. The blood oxygen concentration is obtained by substituting R in Formula (2).

In the example shown in FIG. 4A, the first output signal $V_{out1}$ and the second output signal $V_{out2}$ are obtained using the resistor 251 and the resistor 252. As long as the signal that is output is appropriately processable by the signal processor 903, the first output signal $V_{out1}$ and the second output signal $V_{out2}$ may be obtained using another configuration.

According to the first embodiment, the first photoelectric conversion layer 231 and the second photoelectric conversion layer 232 are stacked in the first direction. The light sensor 2000 can be more compact by employing such a configuration.

According to the first embodiment, the first photoelectric conversion layer 231 and the second photoelectric conversion layer 232 are stacked in the first direction; and at least a portion of the light emitter 1000 and at least a portion of the light sensor 2000 overlap in the first direction. By employing such a configuration, compared to the case where the first photoelectric conversion layer 231 and the second photoelectric conversion layer 232 are arranged in the second direction or the third direction, the difference between the optical path length of the light 121a and the optical path length of the light 121b can be reduced as shown in FIG. 5A. Or, by employing such a configuration, the likelihood that the light 121a and the light 121b will be incident on the same blood vessel can be increased as shown in FIG. 5B. As a result, the measurement sensitivity of the blood oxygen concentration can be increased.

According to the first embodiment, by applying a constant voltage between the first electrode 111 and the second electrode 112, the light that is radiated from the first light emitting layer 121 can be sensed by the first photoelectric conversion layer 231 and the second photoelectric conversion layer 232 that are stacked. Therefore, compared to a configuration in which a pulse voltage is applied between the first electrode 111 and the second electrode 112, the number of parts necessary for the sensor is lower; and the system can be simplified.

Examples of each component will now be described.

The substrate 101 and the substrate 201 include, for example, glass.

The first electrode 111 includes, for example, at least one of aluminum, silver, or gold. The first electrode 111 includes, for example, an alloy of magnesium and silver.

The second electrode 112 includes, for example, ITO (Indium Tin Oxide). The second electrode 112 may include, for example, a conductive polymer such as PEDOT:PSS, etc. The second electrode 112 may include, for example, a metal (including, for example, at least one of aluminum or silver). In the case where the second electrode 112 includes a metal, it is desirable for the thickness of the second electrode 112 in the first direction to be 5 to 20 nm.

The first light emitting layer 121 includes, for example, at least one of Alq3 (tris(8-hydroxyquinolinolato)aluminum), F8BT (poly(9,9-dioctylfluorene-co-benzothiadiazole), PPV (polyparaphenylene vinylene), RO-PPV (alkoxy-substituted PPV), or PF (polyfluorene).

Or, the first light emitting layer 121 may include a host material and a dopant material.

The host material includes, for example, at least one of CBP (4,4'-N,N'-bis dicarbazolyl-biphenyl), BCP (2,9-dimethyl-4,7 diphenyl-1,10-phenanthroline), TPD (2,9-dimethyl-4,7 diphenyl-1,10-phenanthroline), PVK (polyvinyl carbazole), or PPT (poly(3-phenylthiophene)).

The dopant material includes, for example, at least one of Flrpic (iridium(III)-bis(4,6-di-fluorophenyl)-pyridinate-N, C2'-picolinate), Ir(ppy)3 (tris(2-phenylpyridine)iridium), Flr6 (bis(2,4-difluorophenylpyridinato)-tetrakis(1-pyrazolyl)borate-iridium(III)), Ir(MDQ)2(acac), PtOEP, Rubrene, Ir(Piq)3, or DCM.

The configuration of the first electrode 111, the configuration of the first light emitting layer 121, and the configuration of the second electrode 112 in a plane perpendicular to the first direction are, for example, polygons (of which the corners may be curves) or circles (including flattened circles). These configurations are arbitrary.

The third electrode 213 includes, for example, at least one of aluminum, silver, or gold. The third electrode 213 includes, for example, an alloy of magnesium and silver. The fourth electrode 214 and the fifth electrode 215 include, for example, ITO. The fourth electrode 214 and the fifth electrode 215 may include metals such as aluminum, silver, etc. In the case where the fourth electrode 214 and the fifth electrode 215 include metals, it is desirable for the thicknesses of these electrodes in the first direction to be 5 to 20 nm.

The first photoelectric conversion layer 231 and the second photoelectric conversion layer 232 include, for example, at least one of a porphyrin cobalt complex, a coumarin derivative, fullerene, a fullerene derivative, a fluorene compound, a pyrazole derivative, a quinacridone derivative, a perylene bisimide derivative, an oligothiophene derivative, a subphthalocyanine derivative, a rhodamine compound, a ketocyanine derivative, a phthalocyanine derivative, a squarylium derivative, or a subnaphthalocyanine derivative. The material included in the first photoelectric conversion layer 231 is different from the material included in the second photoelectric conversion layer 232.

For example, the porphyrin cobalt complex, the coumarin derivative, fullerene, the derivative of fullerene, the fluorene compound, and the pyrazole derivative selectively absorb blue light having a wavelength of 440 nm to 490 nm.

For example, the quinacridone derivative, the perylene bisimide derivative, the oligothiophene derivative, the subphthalocyanine derivative, the rhodamine compound, and the ketocyanine derivative selectively absorb green light having a wavelength of 490 nm to 600 nm.

For example, the phthalocyanine derivative, the squarylium derivative, and the subnaphthalocyanine derivative selectively absorb red light having a wavelength of 600 nm to 800 nm.

For example, the organic substances included in these photoelectric conversion layers are selected so that the color of the light absorbed by the first photoelectric conversion layer 231 is different from the color of the light absorbed by the second photoelectric conversion layer 232.

Figure 6:
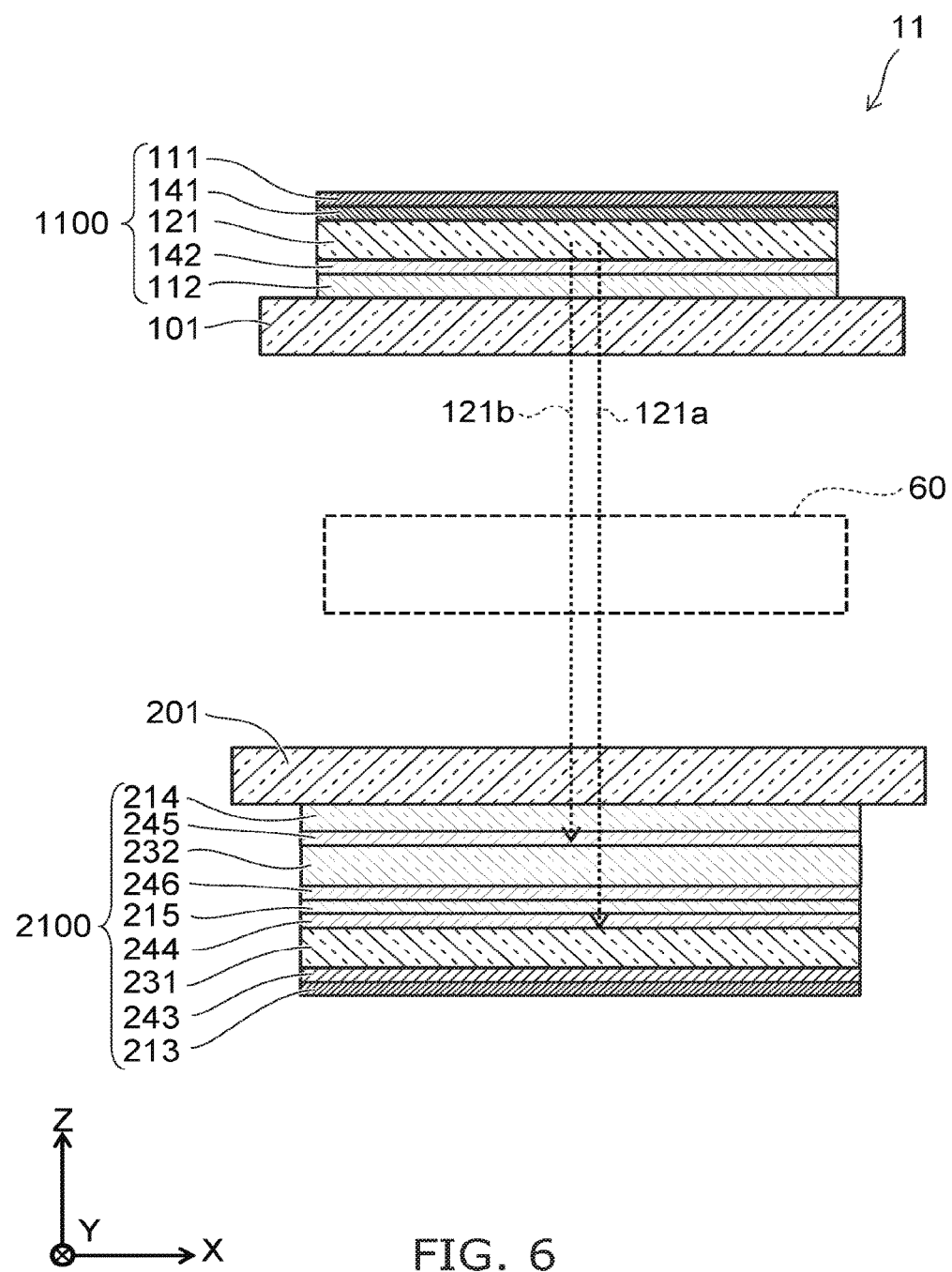
FIG. 6 is a schematic cross-sectional view showing another example of the sensor according to the first embodiment.

FIG. 6 is a schematic cross-sectional view showing another example of the sensor according to the first embodiment. As in the sensor 11 shown in FIG. 6, a first layer 141 and a second layer 142 may be further provided in a light emitter 1100. The first layer 141 is provided between the first electrode 111 and the first light emitting layer 121. The second layer 142 is provided between the second electrode 112 and the first light emitting layer 121.

As in a light sensor 2100 shown in FIG. 6, a third layer 243, a fourth layer 244, the fifth layer 245, and a sixth layer 246 may be further provided. The third layer 243 is provided between the third electrode 213 and the first photoelectric conversion layer 231. The fourth layer 244 is provided between the fifth electrode 215 and the first photoelectric conversion layer 231. The fifth layer 245 is provided between the fourth electrode 214 and the second photoelectric conversion layer 232. The sixth layer 246 is provided between the fifth electrode 215 and the second photoelectric conversion layer 232.

The first layer 141 includes, for example, a carrier injection layer. In the example shown in FIG. 6, the carrier injection layer may function as an electron injection layer. The first layer 141 may include a carrier transport layer. In the example shown in FIG. 6, the carrier transport layer may function as an electron transport layer. The first layer 141 may include a layer that functions as a carrier injection layer and a layer that functions as a carrier transport layer.

The first layer 141 includes, for example, at least one of Alq3, BAlq, POPy2, Bphen, or 3TPYMB. In the case where the first layer 141 includes at least one of these materials, the first layer 141 functions as an electron transport layer.

Or, the first layer 141 includes, for example, at least one of LiF, CsF, Ba, or Ca. In the case where the first layer 141 includes at least one of these materials, the first layer 141 functions as an electron injection layer.

The second layer 142 includes, for example, a carrier injection layer. In the example shown in FIG. 6, the carrier injection layer may function as a hole injection layer. The second layer 142 may include a carrier transport layer. In the example shown in FIG. 6, the carrier transport layer may function as a hole transport layer. The second layer 142 may include a layer that functions as a carrier injection layer and a layer that functions as a carrier transport layer.

The second layer 142 includes, for example, at least one of α-NPD, TAPC, m-MTDATA, TPD, or TCTA. In the case where the second layer 142 includes at least one of these materials, the second layer 142 functions as a hole transport layer.

Or, the second layer 142 includes, for example, at least one of PEDPOT:PPS, CuPc, or $MoO_3$. In the case where the second layer 142 includes at least one of these materials, the second layer 142 functions as a hole injection layer.

The third layer 243 and the fifth layer 245 include, for example, at least one of an electron blocking layer that obstructs the flow of electrons or a hole extraction layer (a trap layer) that allows holes to flow easily. These layers also may function as exciton blocking layers for trapping the excitons generated by the first photoelectric conversion layer 231 and the second photoelectric conversion layer 232.

It is desirable for the third layer 243 and the fifth layer 245 to include, for example, a hole-accepting material. As the hole-accepting material, for example, a triarylamine compound, a benzidine compound, a pyrazoline compound, a styrylamine compound, a hydrazone compound, a triphenylmethane compound, a carbazole compound, a thiophene compound, a phthalocyanine compound, a condensed aromatic compound, etc., may be used. As the condensed aromatic compound, for example, a naphthalene derivative, an anthracene derivative, a tetracene derivative, a pentacene derivative, a pyrene derivative, a perylene derivative, etc., may be used.

The material that is included in the third layer 243 may be different from the material included in the fifth layer 245.

The fourth layer 244 and the sixth layer 246 include, for example, at least one of a hole blocking layer that obstructs the flow of holes or an electron extraction layer (a trap layer) that allows electrons to flow easily. These layers also may function as exciton blocking layers for trapping the excitons generated by the first photoelectric conversion layer 231 and the second photoelectric conversion layer 232.

It is desirable for the fourth layer 244 and the sixth layer 246 to include, for example, an electron-accepting material. As the electron-accepting material, for example, an oxadiazole derivative, a triazole compound, an anthraquinodimethane derivative, a diphenylquinone derivative, bathocuproine, a bathocuproine derivative, bathophenanthroline, a bathophenanthroline derivative, a 1,4,5,8-naphthalenetetracarboxylic diimide derivative, naphthalene-1,4,5,8-tetracarboxylic dianhydride, etc., may be used.

The material that is included in the fourth layer 244 may be different from the material included in the sixth layer 246.

The function of the third layer 243 and the function of the fourth layer 244 described above may be reversed. The function of the fifth layer 245 and the function of the sixth layer 246 may be reversed.

Figure 7:
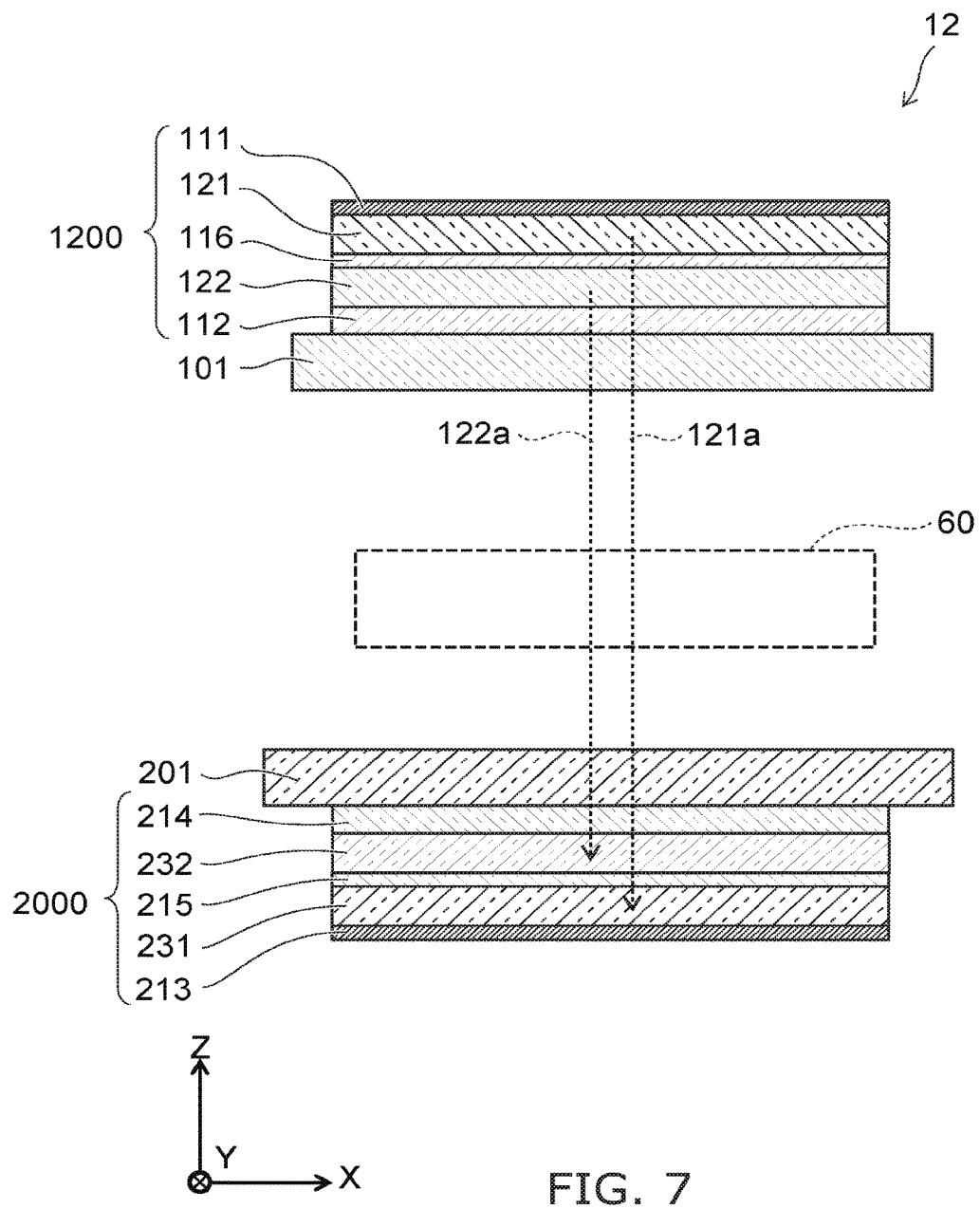
FIG. 7 is a schematic cross-sectional view showing another example of the sensor according to the first embodiment.

FIG. 7 is a schematic cross-sectional view showing another example of the sensor according to the first embodiment.

The sensor 12 includes a light emitter 1200 and the light sensor 2000. As shown in FIG. 7, the light emitter 1200 includes the first electrode 111, the second electrode 112, a sixth electrode 116, the first light emitting layer 121, and a second light emitting layer 122. The sixth electrode 116 is provided between the second electrode 112 and the first light emitting layer 121. The second light emitting layer 122 is provided between the second electrode 112 and the sixth electrode 116.

The second light emitting layer 122 includes, for example, an organic substance. The second light emitting layer 122 may include an organic film containing an organic substance. The second light emitting layer 122 includes, for example, at least one of Alq3 (tris(8-hydroxyquinolinolato) aluminum), F8BT (poly(9,9-dioctylfluorene-co-benzothiadiazole), PPV (polyparaphenylene vinylene), RO-PPV (alkoxy-substituted PPV), or PF (polyfluorene).

Or, the second light emitting layer 122 may include a host material and a dopant material. The host material includes, for example, at least one of CBP (4,4'-N,N'-bis dicarbazolyl-biphenyl), BCP (2,9-dimethyl-4,7 diphenyl-1,10-phenanthroline), TPD (2,9-dimethyl-4,7 diphenyl-1,10-phenanthroline), PVK (polyvinyl carbazole), or PPT (poly(3-phenylthiophene)). The dopant material includes, for example, at least one of Flrpic (iridium(III)-bis(4,6-di-fluorophenyl)-pyridinate-N,C2'-picolinate), Ir(ppy)3 (tris(2-phenylpyridine)iridium), Flr6 (bis(2,4-difluorophenylpyridinato)-tetrakis(1-pyrazolyl)borate-iridium(III)), Ir(MDQ)2(acac), PtOEP, Rubrene, Ir(Piq)3, or DCM.

The light that is radiated from the first light emitting layer 121 and the second light emitting layer 122 is, for example, visible light. For example, the light that is radiated from these light emitting layers is one of red, orange, yellow, green, or blue light, or a combination of such light. The light that is radiated from the first light emitting layer 121 and the second light emitting layer 122 may be ultraviolet light or infrared light. It is desirable for the spectral width of the light radiated from the first light emitting layer 121 and the second light emitting layer 122 to be as wide as possible. The full width at half maximum of the spectrum is, for example, 50 nm or more.

The material of the first photoelectric conversion layer 231 and the material of the second photoelectric conversion layer 232 are selected so that the wavelength of the light absorbed mainly by the first photoelectric conversion layer 231 is different from the wavelength of the light absorbed mainly by the second photoelectric conversion layer 232. Of the light radiated from the first light emitting layer 121 or the second light emitting layer 122, the first photoelectric conversion layer 231 selectively absorbs the light in the absorption wavelength region of the first photoelectric conversion layer 231. Of the light radiated from the first light emitting layer 121 or the second light emitting layer 122, the second photoelectric conversion layer 232 selectively absorbs the light in the absorption region of the second photoelectric conversion layer 232.

The difference between the wavelength of the light selectively absorbed by the first photoelectric conversion layer 231 and the wavelength of the light selectively absorbed by the second photoelectric conversion layer 232 is, for example, 50 nm or more. More desirably, the difference is 100 nm or more.

The material of the first light emitting layer 121 and the material of the second light emitting layer 122 may be selected so that the peak wavelength of the light 121a radiated from the first light emitting layer 121 is different from the peak wavelength of light 122a radiated from the second light emitting layer 122. As shown in FIG. 7, for example, the peak wavelength region of the light 121a radiated from the first light emitting layer 121 is absorbed mainly by the first photoelectric conversion layer 231. The peak wavelength region of the light 122a radiated from the second light emitting layer 122 is absorbed mainly by the second photoelectric conversion layer 232. The difference between the peak wavelength of the light 121a and the peak wavelength of the light 122a is, for example, 50 nm or more. The material of the first light emitting layer 121 and the material of the second light emitting layer 122 are selected so that the peak wavelength of the light 121a and the peak wavelength of the light 122a are included in the wavelength region where the light sensor 2000 has sensing sensitivity.

Figure 8:
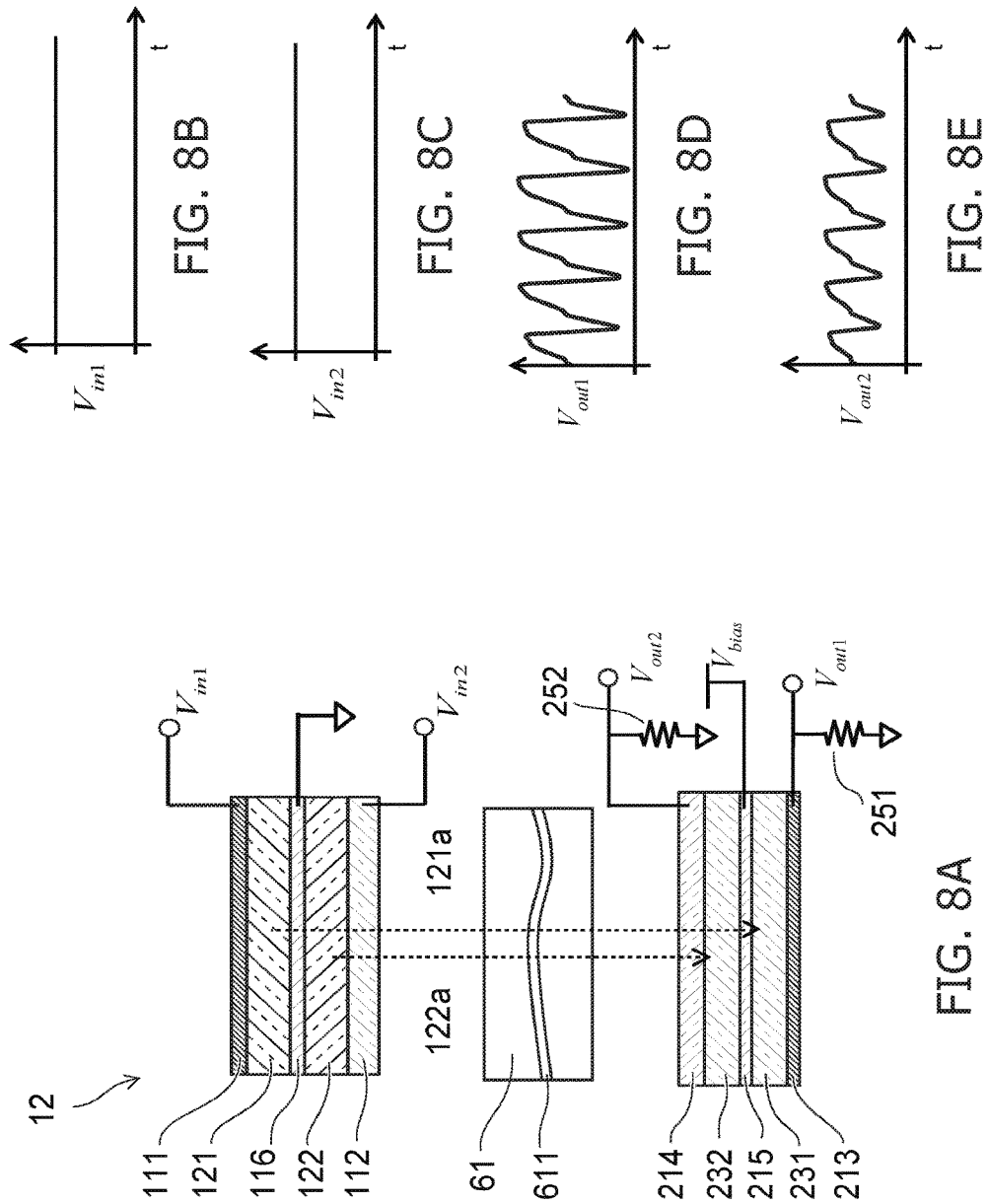
FIG. 8A to FIG. 8E are schematic views showing a method for measuring the blood oxygen concentration using another sensor according to the first embodiment.

FIG. 8A to FIG. 8E are schematic views showing a method for measuring the blood oxygen concentration using another sensor according to the first embodiment. In FIG. 8B to FIG. 8E, the horizontal axis is the time t. The vertical axis of FIG. 8B is a first input signal $V_{in1}$ input between the first electrode 111 and the sixth electrode 116. The vertical axis of FIG. 8C is a second input signal $V_{in2}$ input between the second electrode 112 and the sixth electrode 116. The vertical axis of FIG. 8D is the first output signal $V_{out1}$ sensed by the first photoelectric conversion layer 231. The vertical axis of FIG. 8E is the second output signal $V_{out2}$ sensed by the second photoelectric conversion layer 232.

FIG. 8A shows the state when the oxygen concentration inside the blood vessel 611 of the finger 61 is measured using the sensor 12. The substrate 101 and the substrate 201 are not shown in FIG. 8A. As shown in FIG. 8B, for example, a constant voltage is applied between the first electrode 111 and the sixth electrode 116. As shown in FIG. 8C, for example, a constant voltage is applied between the second electrode 112 and the sixth electrode 116. The lights 121a and 122a that are radiated from the light emitting layers pass through the blood vessel 611. The light that passes through the blood vessel 611 is absorbed by the first photoelectric conversion layer 231 and the second photoelectric conversion layer 232; and the first output signal $V_{out1}$ and the second output signal $V_{out2}$ are obtained as shown in FIG. 8D and FIG. 8E. The oxygen concentration of the blood is measured using these output signals.

FIG. 9, FIG. 10, FIG. 11, and FIG. 12 are schematic cross-sectional views showing other examples of the sensor according to the first embodiment.

Figure 9:
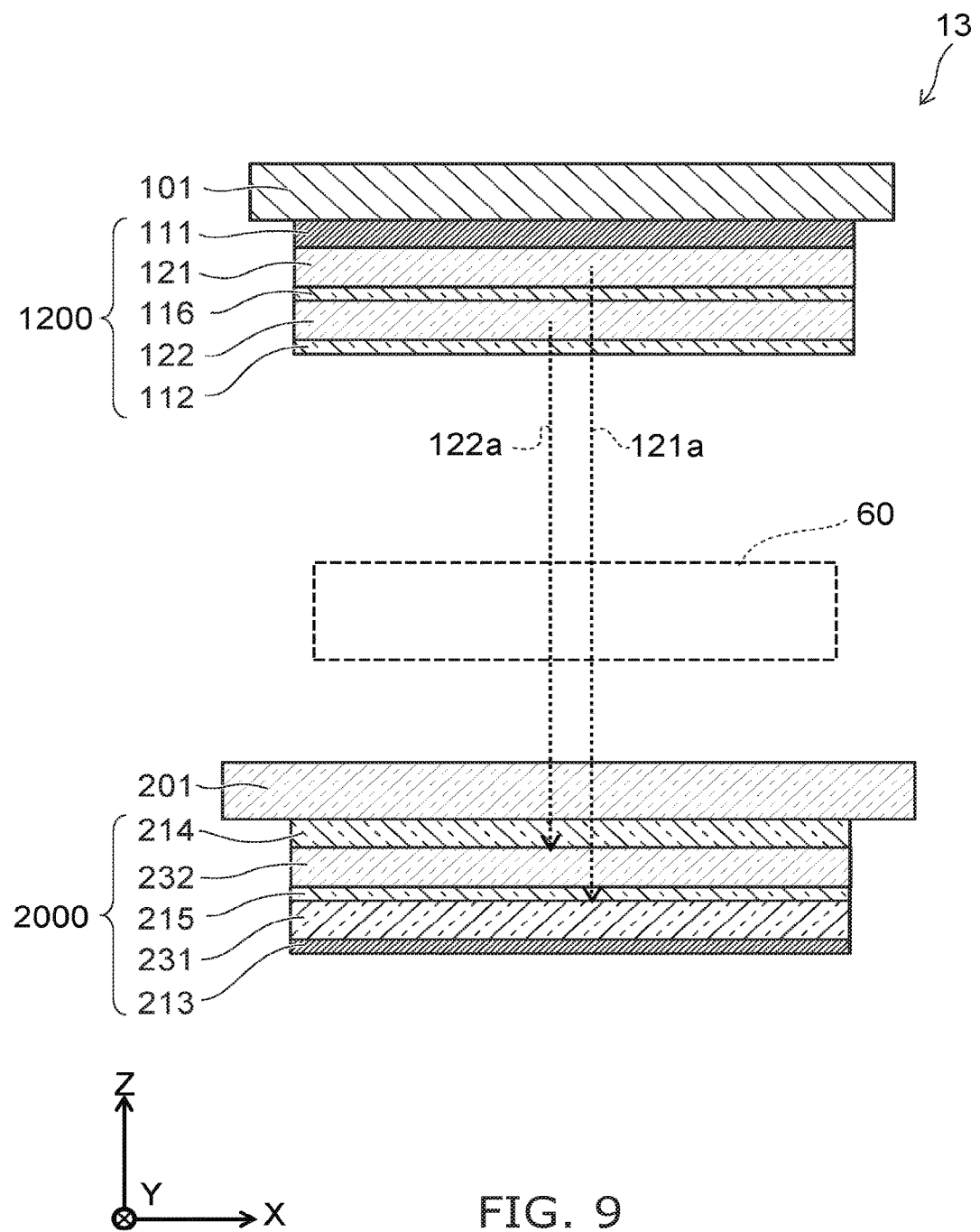
FIG. 9, FIG. 10, FIG. 11, and FIG. 12 are schematic cross-sectional views showing other examples of the sensor according to the first embodiment.

In the sensor 13 shown in FIG. 9, the light emitter 1200 is provided between at least a portion of the substrate 101 and at least a portion of the substrate 201. At least a portion of the substrate 201 is provided between the light emitter 1200 and the light sensor 2000. The light 121a that is radiated from the first light emitting layer 121 passes through the sixth electrode 116 and the second electrode 112 and is incident on the measurement object 60.

Figure 10:
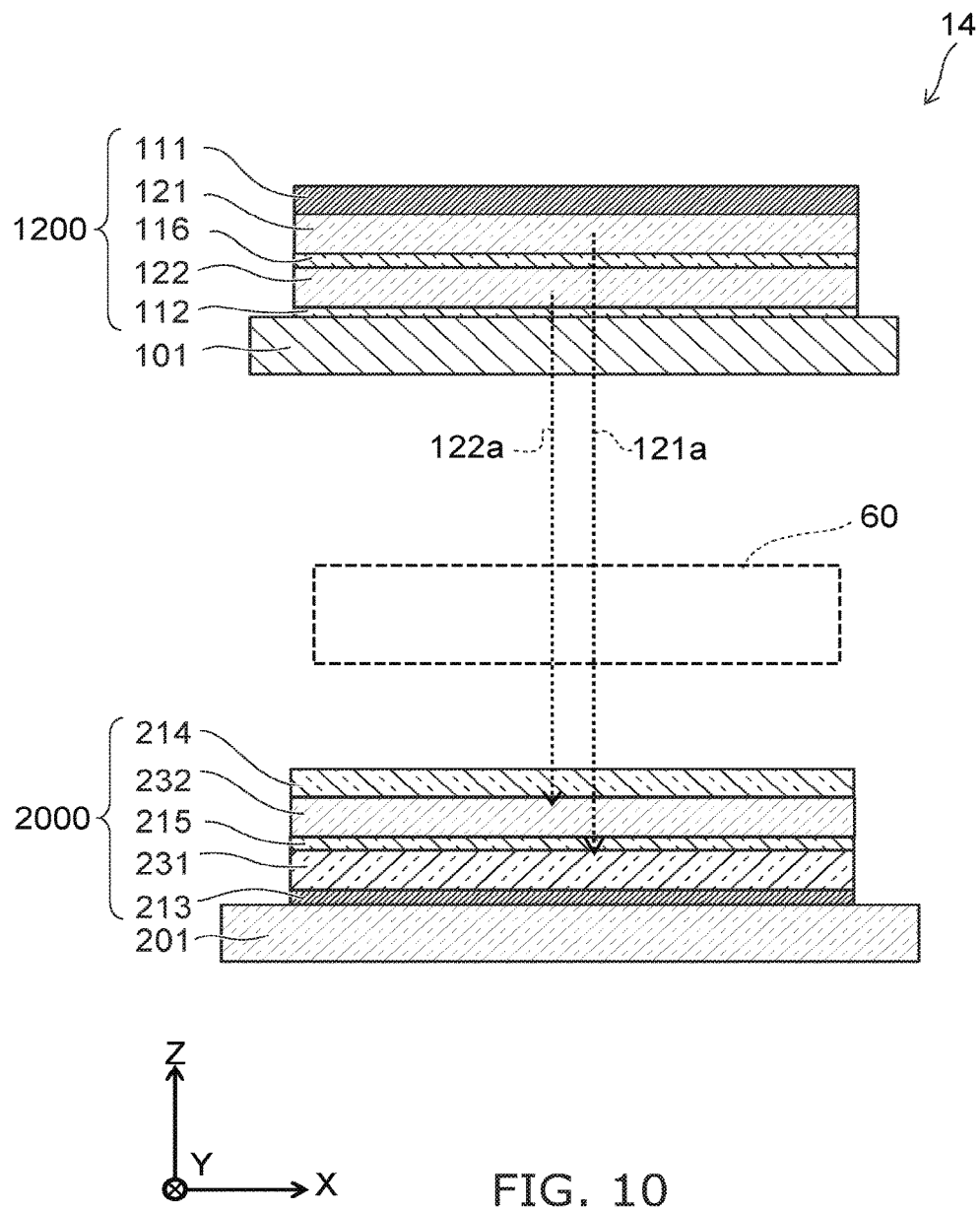

In the sensor 14 shown in FIG. 10, the light sensor 2000 is provided between at least a portion of the substrate 101 and at least a portion of the substrate 201. At least a portion of the substrate 101 is provided between the light emitter 1200 and the light sensor 2000.

Figure 11:
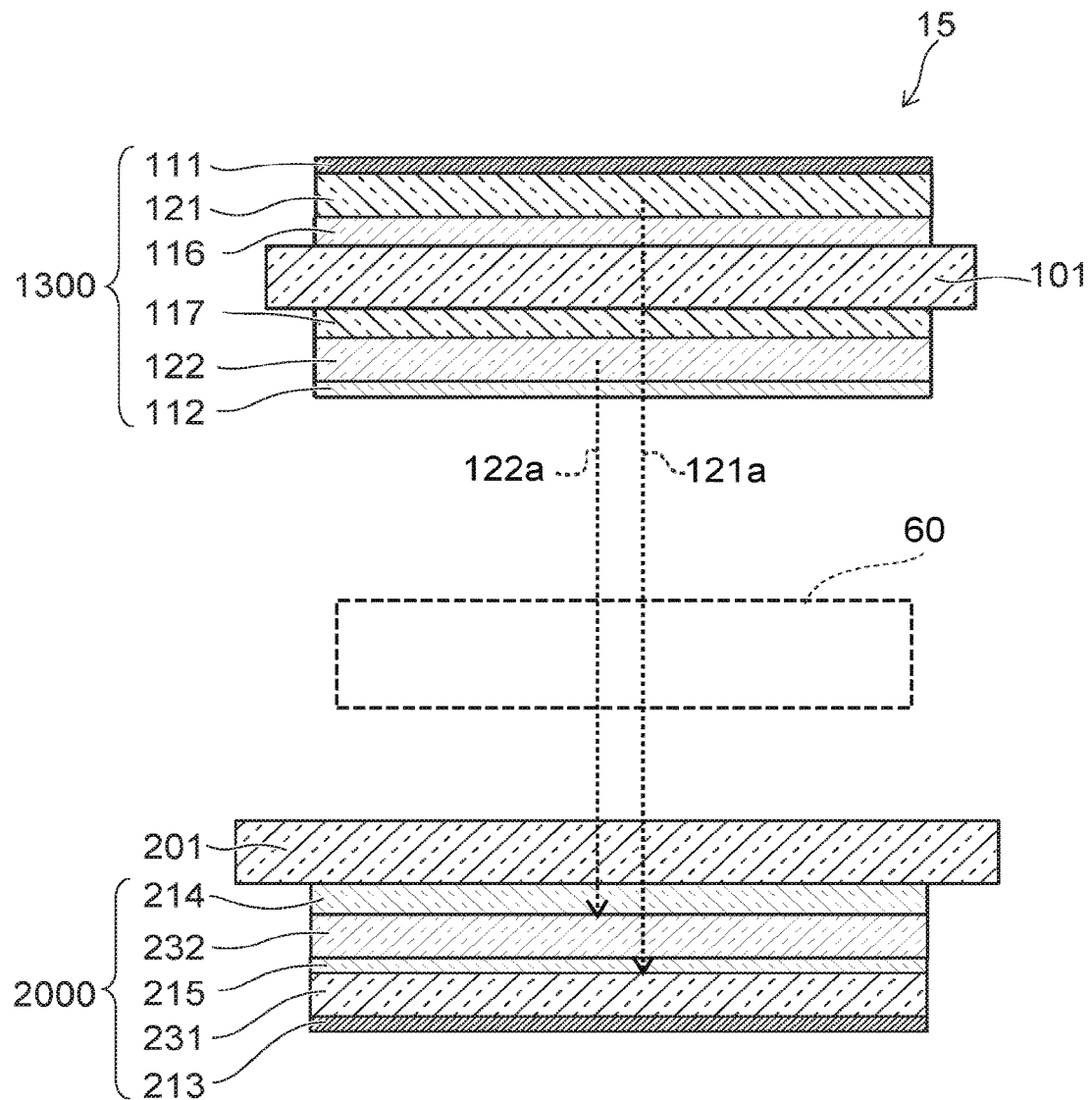

The sensor 15 shown in FIG. 11 includes a light emitter 1300 and the light sensor 2000. In the sensor 15, a portion of the substrate 101 is provided between the first electrode 111 and the second electrode 112.

As shown in FIG. 11, the first light emitting layer 121 is provided between the first electrode 111 and a portion of the substrate 101. The sixth electrode 116 is provided between the first light emitting layer 121 and a portion of the substrate 101.

The second light emitting layer 122 is provided between the second electrode 112 and a portion of the substrate 101. A seventh electrode 117 is provided between the second light emitting layer 122 and a portion of the substrate 101.

The second light emitting layer 122 is provided between at least a portion of the substrate 101 and at least a portion of the substrate 201. At least a portion of the substrate 201 is provided between the light emitter 1300 and the light sensor 2000. The light 121a that is radiated from the first light emitting layer 121 passes through the sixth electrode 116, the substrate 101, the seventh electrode 117, the second light emitting layer 122, and the second electrode 112 and is incident on the measurement object 60.

Figure 12:
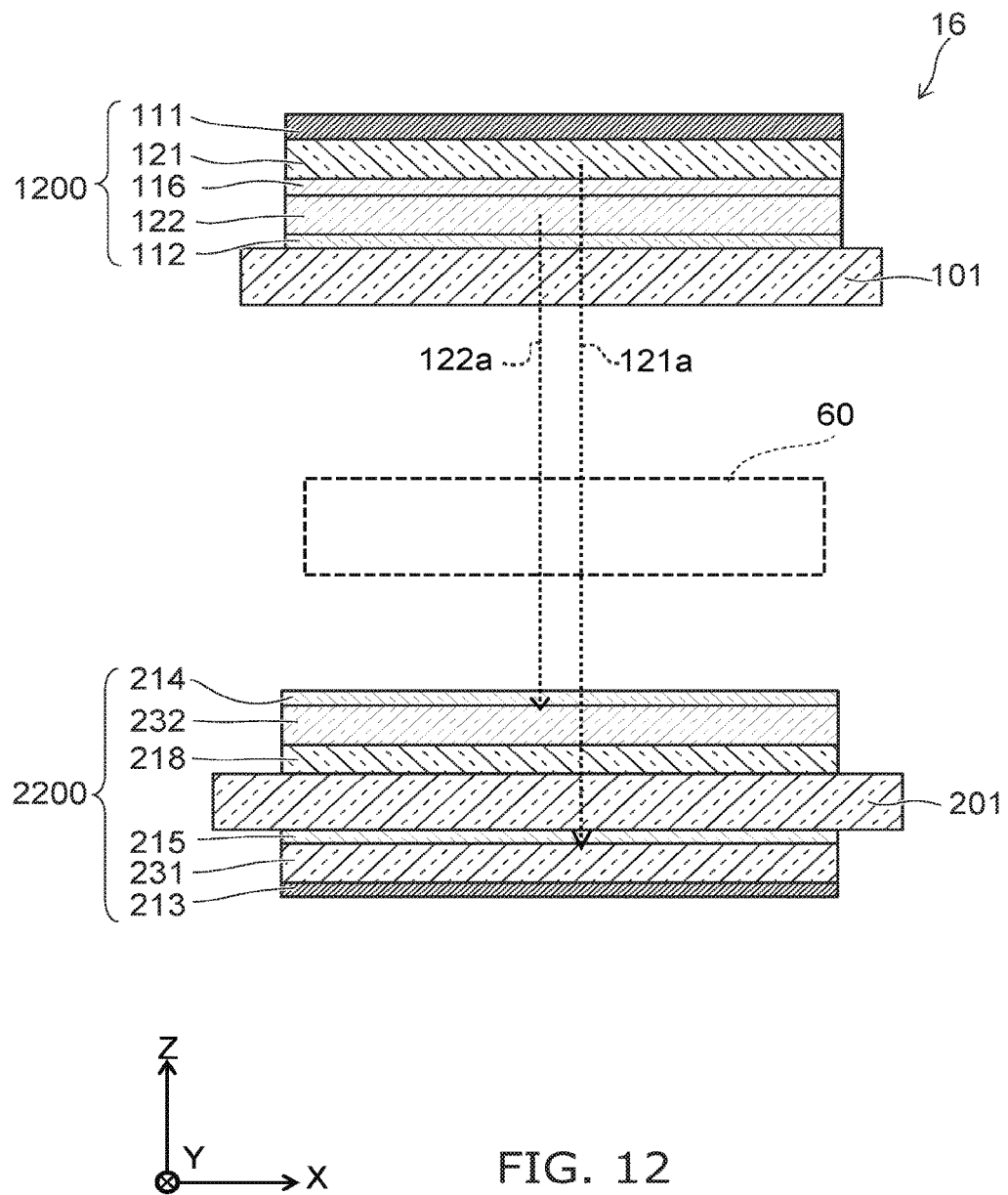

The sensor 16 shown in FIG. 12 includes the light emitter 1200 and a light sensor 2200. In the sensor 16, a portion of the substrate 201 is provided between the third electrode 213 and the fourth electrode 214.

As shown in FIG. 12, the fifth electrode 215 is provided between the third electrode 213 and a portion of the substrate 201. The first photoelectric conversion layer 231 is provided between the third electrode 213 and the fifth electrode 215.

An eighth electrode 218 is provided between the fourth electrode 214 and a portion of the substrate 201. The second photoelectric conversion layer 232 is provided between the fourth electrode 214 and the eighth electrode 218.

The lights 121a and 122a that are radiated from the first light emitting layer 121 and the second light emitting layer 122 pass through the second electrode 112 and the substrate 101 and are incident on the measurement object 60.

Or, the sensor may include the light emitter 1300 shown in FIG. 11 and the light sensor 2200 shown in FIG. 12.

As in the sensor 10 shown in FIG. 2 and FIG. 3, the other sensors according to the first embodiment described above may further include the processor 900 in addition to the light emitter and sensor.

Second Embodiment

Figure 13:
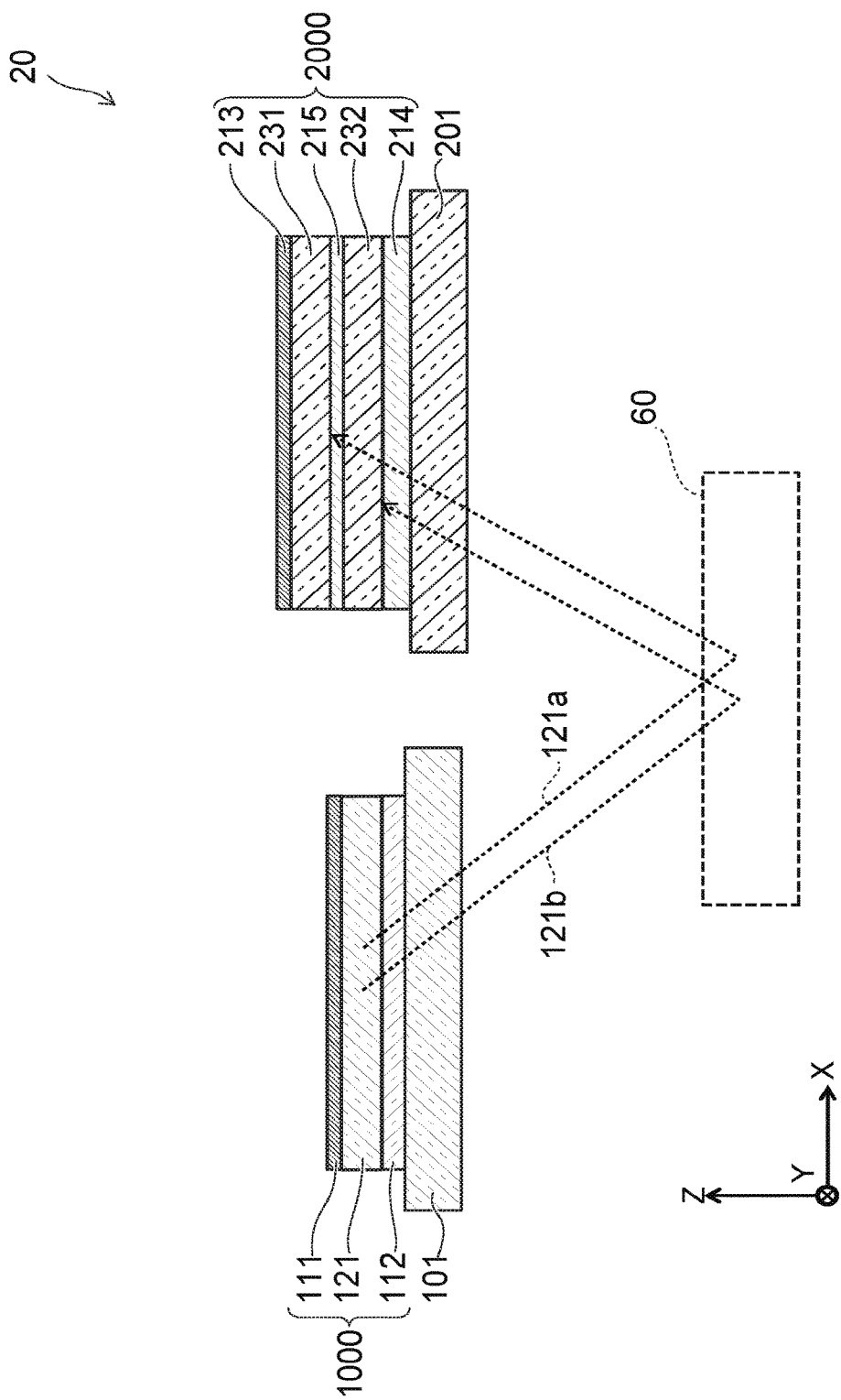
FIG. 13 is a schematic cross-sectional view showing an example of a sensor according to a second embodiment.

FIG. 13 is a schematic cross-sectional view showing an example of a sensor according to a second embodiment.

As shown in FIG. 13, the sensor 20 includes the light emitter 1000 and the light sensor 2000.

The light emitter 1000 includes the first electrode 111, the second electrode 112, and the first light emitting layer 121. The light sensor 2000 includes the third electrode 213, the fourth electrode 214, the fifth electrode 215, the first photoelectric conversion layer 231, and the second photoelectric conversion layer 232.

At least a portion of the light emitter 1000 and at least a portion of the light sensor 2000 overlap in the second direction.

Instead of the light emitter 1000, one of the light emitters 1100 to 1300 may be used in the sensor 20. Instead of the light sensor 2000, the light sensor 2100 or 2200 may be used in the sensor 20.

The light 121a and the light 121b that are radiated from the first light emitting layer 121 are reflected or scattered by the measurement object 60 and are incident on the first photoelectric conversion layer 231 and the second photoelectric conversion layer 232. Because the light that is reflected or scattered by the measurement object 60 includes the signal of the measurement object 60, the information relating to the measurement object 60 can be obtained by sensing the light.

In the embodiment as well, a compact sensor is possible because the first photoelectric conversion layer 231 and the second photoelectric conversion layer 232 are stacked in the first direction. As in the sensor 10 shown in FIG. 2 and FIG. 3, the sensor 20 may further include the processor 900 in addition to the light emitter 1000 and the light sensor 2000.

Third Embodiment

Figure 14:
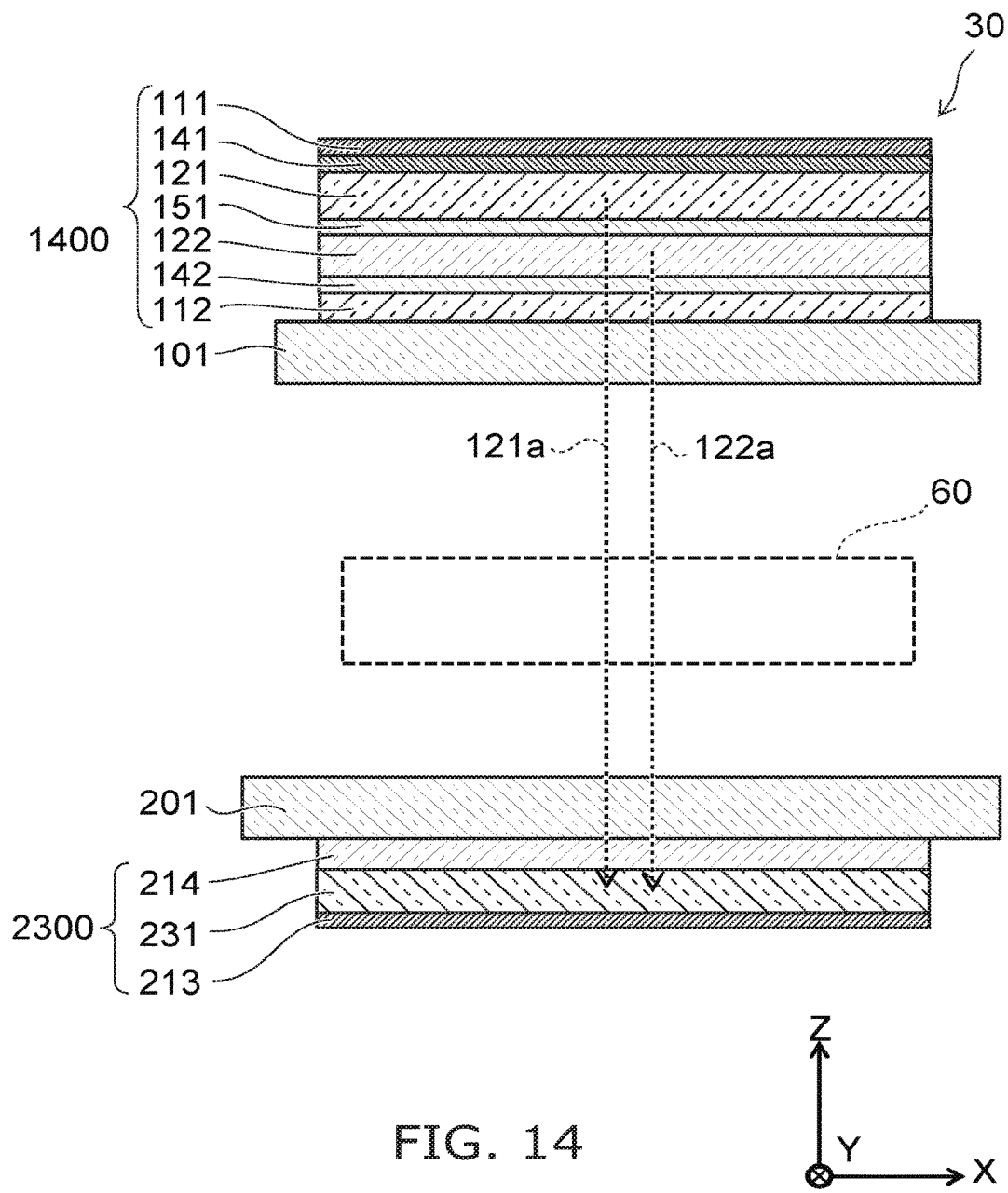
FIG. 14 is a schematic cross-sectional view showing an example of a sensor according to a third embodiment.

FIG. 14 is a schematic cross-sectional view showing an example of a sensor according to a third embodiment.

As shown in FIG. 14, the sensor 30 includes a light emitter 1400 and a light sensor 2300. For example, the measurement object 60 is provided between at least a portion of the light emitter 1400 and at least a portion of the light sensor 2300 in the first direction.

The light emitter 1400 includes the first electrode 111, the second electrode 112, the first light emitting layer 121, the second light emitting layer 122, the first layer 141, the second layer 142, and an exciton diffusion layer 151 (an intermediate layer). The first layer 141 is provided between the first electrode 111 and the second electrode 112. The first light emitting layer 121 is provided between the first layer 141 and the second electrode 112. The exciton diffusion layer 151 is light-transmissive and is provided between the first light emitting layer 121 and the second electrode 112. The second light emitting layer 122 is provided between the exciton diffusion layer 151 and the second electrode 112. The second layer 142 is provided between the second light emitting layer 122 and the second electrode 112. For example, the light emitter 1400 is provided on the substrate 101.

The light sensor 2300 includes the third electrode 213, the fourth electrode 214, and the first photoelectric conversion layer 231. For example, the light sensor 2300 is provided on the substrate 201.

The peak wavelength of the light 121a radiated from the first light emitting layer 121 is different from the peak wavelength of the light 122a radiated from the second light emitting layer 122. The light 121a and the light 122a are absorbed by the first photoelectric conversion layer 231.

FIG. 15, FIG. 16, and FIGS. 17A to 17B are schematic views showing characteristics of the light emitter included in the sensor according to the third embodiment.

Figure 15:
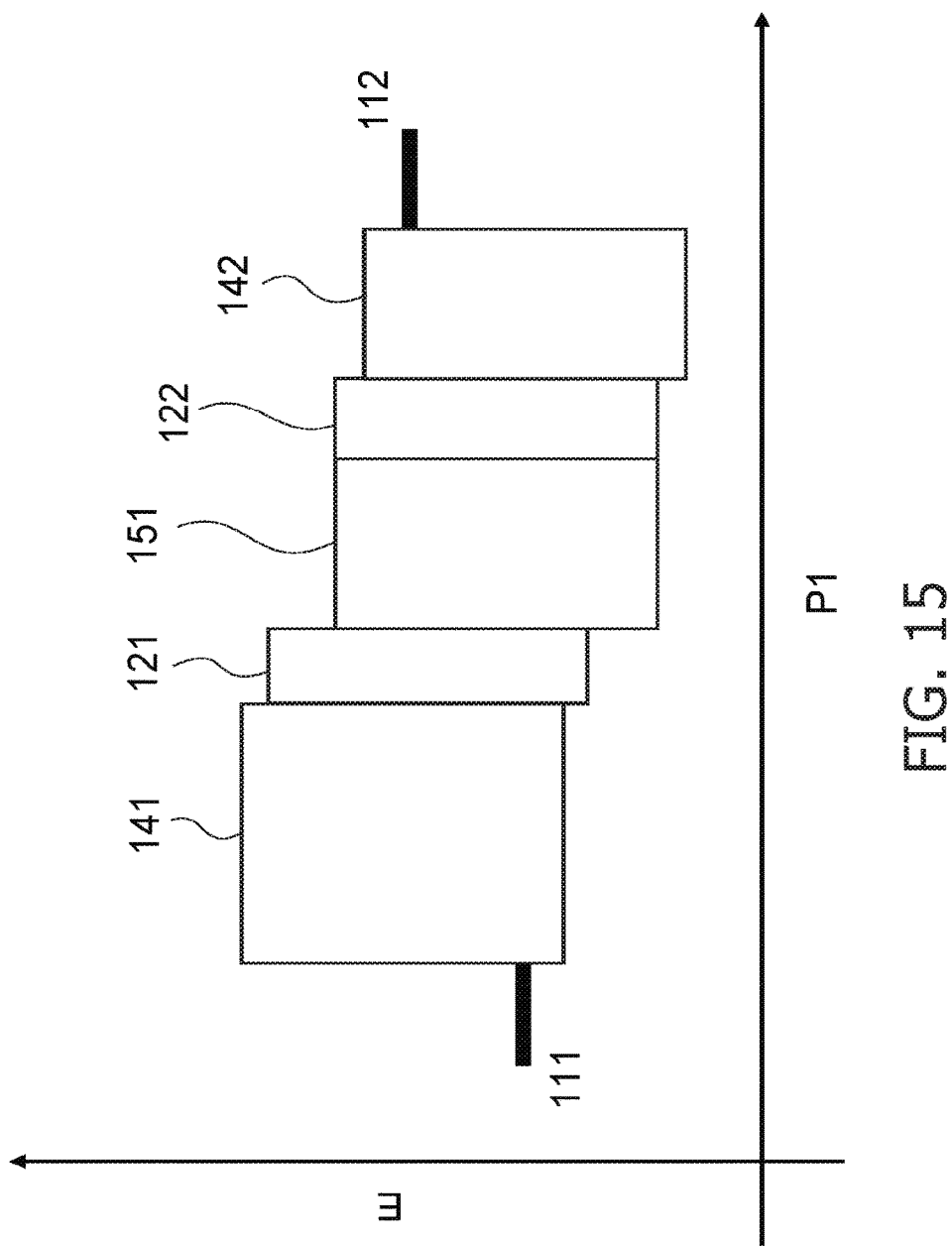
FIG. 15, FIG. 16, and FIGS. 17A to 17B are schematic views showing characteristics of the light emitter included in the sensor according to the third embodiment.
Figure 16:
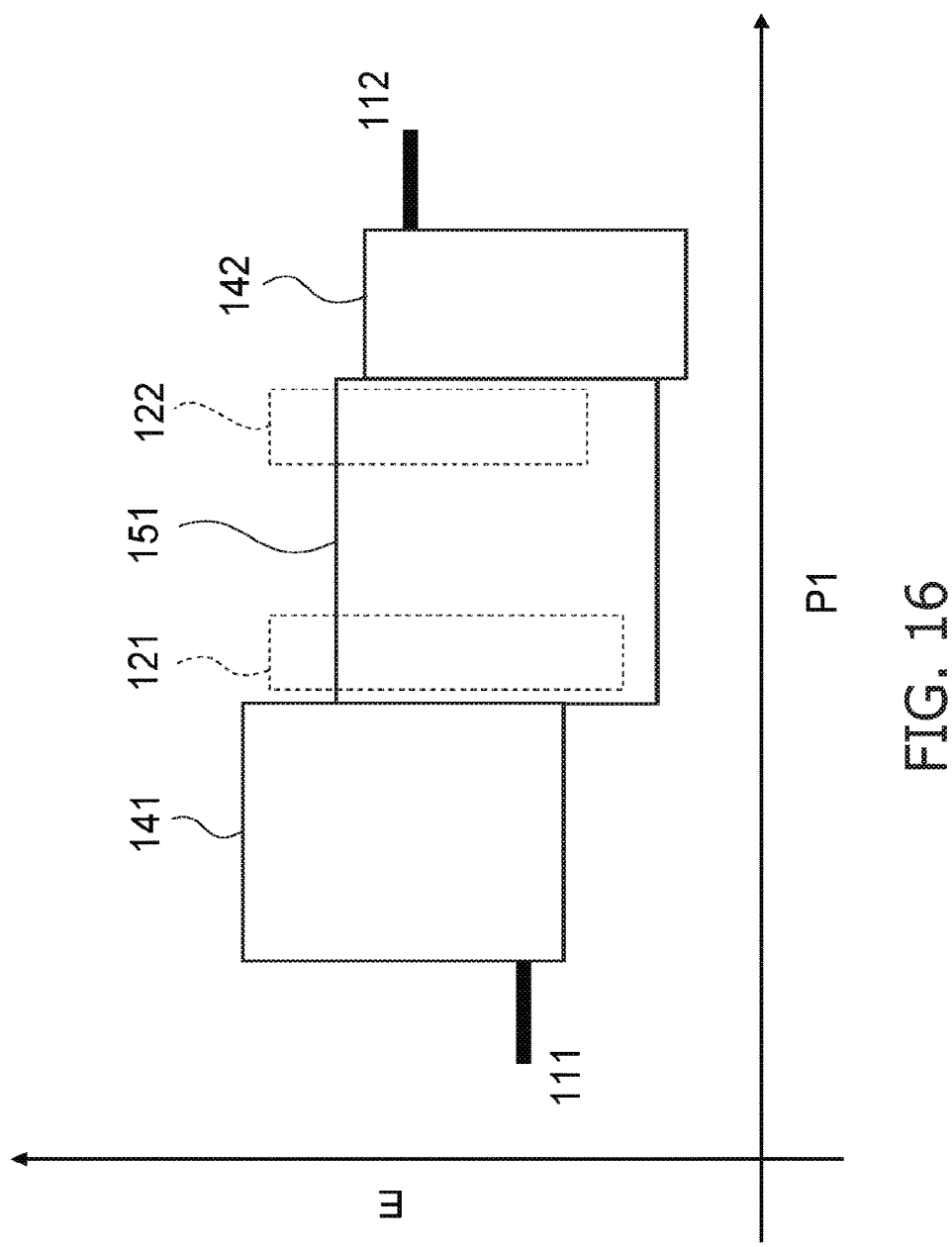

In FIG. 15 and FIG. 16, the horizontal axis is a position P1 in the first direction. In FIG. 15 and FIG. 16, the vertical axis is an energy E at each position.

The bottom side of each of the quadrilaterals included in FIG. 15 and FIG. 16 illustrates the highest occupied molecular orbit (HOMO) or valence band of each component. The upper side of each of the quadrilaterals illustrates the lowest unoccupied molecular orbit (LUMO) or conduction band of each component.

Specifically, FIG. 15 shows the characteristics of the light emitter 1400 in the case where the materials included in the first light emitting layer 121 and the second light emitting layer 122 as the light emitting materials are different from the material included in the exciton diffusion layer 151.

FIG. 16 shows the characteristics of the light emitter 1400 in the case where the materials included as host materials in the first light emitting layer 121 and the second light emitting layer 122 are the same as the material included in the exciton diffusion layer 151; and the first light emitting layer 121 and the second light emitting layer 122 include guest materials in addition to the host materials.

In FIG. 16, the bottom side of each of the quadrilaterals illustrated by the broken lines illustrates the HOMO of each guest material. The upper side of each of the quadrilaterals illustrated by the broken lines illustrates the LUMO of each guest material.

Figure 17A:
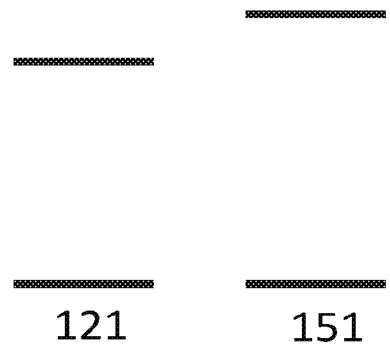
Figure 17B:
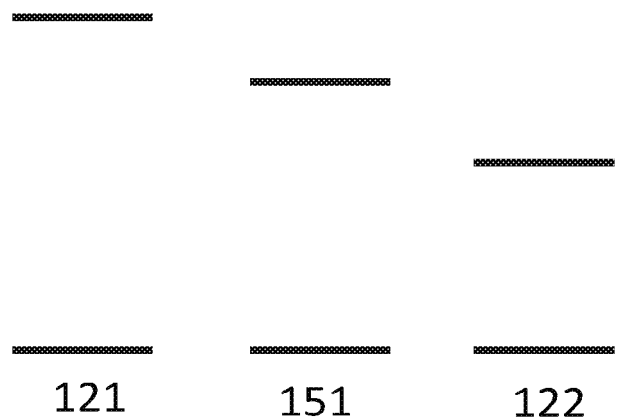

FIG. 17A and FIG. 17B are schematic views showing the energy levels of the light emitting material included in the first light emitting layer 121, the light emitting material included in the second light emitting layer 122, and the material included in the exciton diffusion layer 151. In FIG. 17A and FIG. 17B, the bottom lines illustrate the energy level in the ground state of each material. In FIG. 17A, the top lines illustrate the energy level in the excited singlet state of each material. In FIG. 17B, the top lines illustrate the energy level in the excited triplet state of each material.

When holes and electrons are injected from the first electrode 111 and the second electrode 112, for example, excitons are generated between the first layer 141 and the exciton diffusion layer 151. Light is radiated from the first light emitting layer 121 due to a portion of the excitons that are generated. The other excitons propagate through the exciton diffusion layer 151 and move into the second light emitting layer 122. Light is radiated from the second light emitting layer 122 due to these excitons.

As shown in FIG. 17A, the energy level in the excited singlet state of the light emitting material included in the first light emitting layer 121 is, for example, lower than the energy level in the excited singlet state of the material included in the exciton diffusion layer 151. As shown in FIG. 17B, the energy level in the excited triplet state of the light emitting material included in the second light emitting layer 122 is, for example, lower than the energy level in the excited triplet state of the material included in the exciton diffusion layer 151 and lower than the energy level in the excited triplet state of the light emitting material included in the first light emitting layer 121.

The excitons that are generated between the first layer 141 and the exciton diffusion layer 151 have the excited singlet state or the excited triplet state. By employing the configuration described above, it is possible to cause the first light emitting layer 121 to emit light by the excitons having the excited singlet state and cause the second light emitting layer 122 to emit light by the excitons having the excited triplet state.

According to the configuration of the sensor 30, the two light emitting layers of the first light emitting layer 121 and the second light emitting layer 122 can be caused to emit light even in the case where another electrode is not provided between the first electrode 111 and the second electrode 112. Therefore, the electrical connection between the external circuit and the electrodes included in the light emitter can be simple.

Figure 19A:
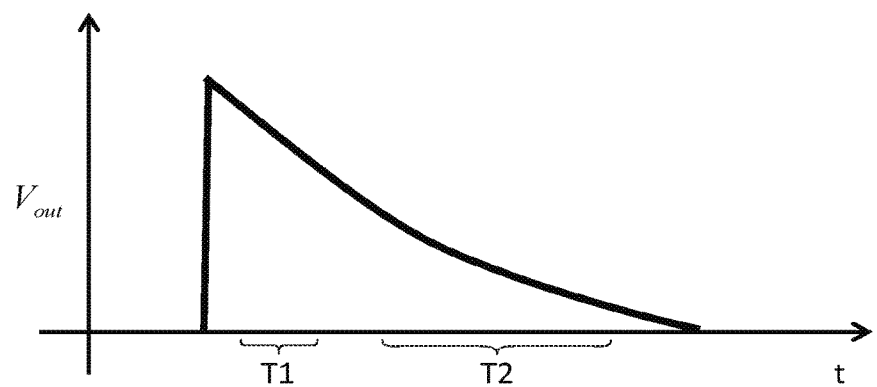
Figure 19B:
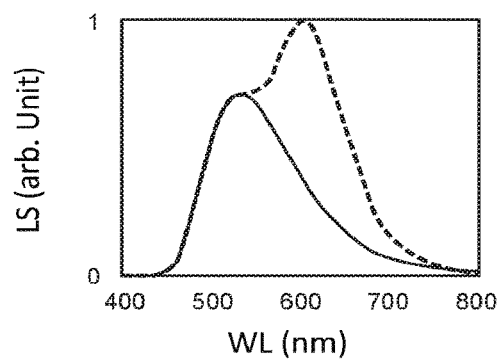
Figure 19C:
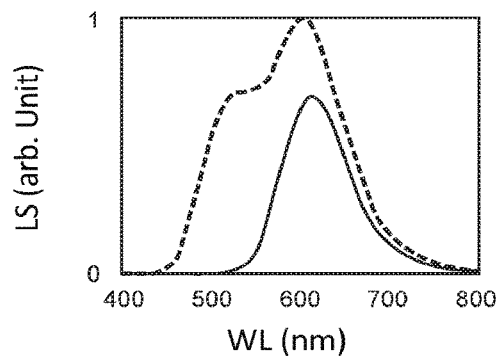

FIG. 18A to FIG. 18C and FIG. 19A to FIG. 19C are schematic views showing the method for measuring the blood oxygen concentration using the sensor according to the third embodiment. In FIG. 18B, FIG. 18C, and FIG. 19A, the horizontal axis is the time t. The vertical axis of FIG. 18B is the input signal $V_{in}$ input between the first electrode 111 and the second electrode 112. In FIG. 18C and FIG. 19A, the vertical axis is an output signal $V_{out}$ sensed by the first photoelectric conversion layer 231. In FIG. 19B and FIG. 19C, the horizontal axis is a wavelength WL. In FIG. 19B and FIG. 19C, the vertical axis is a light intensity LS.

As shown in FIG. 18B, a pulse voltage is applied as the input signal $V_{in}$ between the first electrode 111 and the second electrode 112 of the light emitter 1400. When the voltage is applied between the first electrode 111 and the second electrode 112, light is radiated from the first light emitting layer 121 and the second light emitting layer 122.

At this time, excitons are generated between the first layer 141 and the exciton diffusion layer 151; and a portion of the excitons propagate through the exciton diffusion layer 151 and move into the second light emitting layer 122. Therefore, after the voltage is applied to the first electrode 111 and the second electrode 112, the time for the light to be radiated from the second light emitting layer 122 is different from the time for the light to be radiated from the first light emitting layer 121. As a result, as shown in FIG. 18C, the output signal is largest when the voltage is applied to the first electrode 111 and the second electrode 112 and subsequently decreases gradually.

FIG. 19A is an enlarged portion of the output signal of FIG. 18C. For example, the light that is sensed in an interval T1 shown in FIG. 19A is mainly the light 121a radiated from the first light emitting layer 121. The light that is sensed in an interval T2 shown in FIG. 19A is mainly the light 122a radiated from the second light emitting layer 122.

FIG. 19B shows the signal sensed in the interval T1. FIG. 19C shows the signal sensed in the interval T2. In each figure, the broken line illustrates the entire output signal sensed for the input of one pulse signal. Thus, by sensing each signal of the mutually-different intervals, it is possible to separately obtain the information included in the light 121a and the information included in the light 122a.

The first light emitting layer 121 includes, for example, a material that emits fluorescence; and the second light emitting layer 122 includes, for example, a material that emits phosphorescence. The typical emission lifetime of a fluorescent material is 1 to 100 ns. The typical emission lifetime of a phosphorescent material is 1 to 100 µs. The emission lifetime of the phosphorescent material is greatly different from the emission lifetime of the fluorescent material.

At least one of Alq3 or DCM may be used as the fluorescent material.

At least one of Ir(ppy)3 or Ir(MDQ)2(acac) may be used as the phosphorescent material.

Therefore, when the pulse voltage is applied between the first electrode 111 and the second electrode 112, the light is radiated initially from the light emitting layer including the fluorescent material. Then, after the time corresponding to the emission lifetime of the fluorescent material has elapsed, the light is radiated from the light emitting layer including the phosphorescent material. Therefore, similarly to the example shown in FIG. 19A to FIG. 19C, the information that is included in the light radiated from the first light emitting layer 121 and the information that is included in the light radiated from the second light emitting layer 122 can be obtained separately.

According to the embodiment, a sensor that is more compact is possible because the first light emitting layer 121 and the second light emitting layer 122 are stacked, and because the light that is radiated from each of the light emitting layers is sensed by one photoelectric conversion layer.

Figure 20:
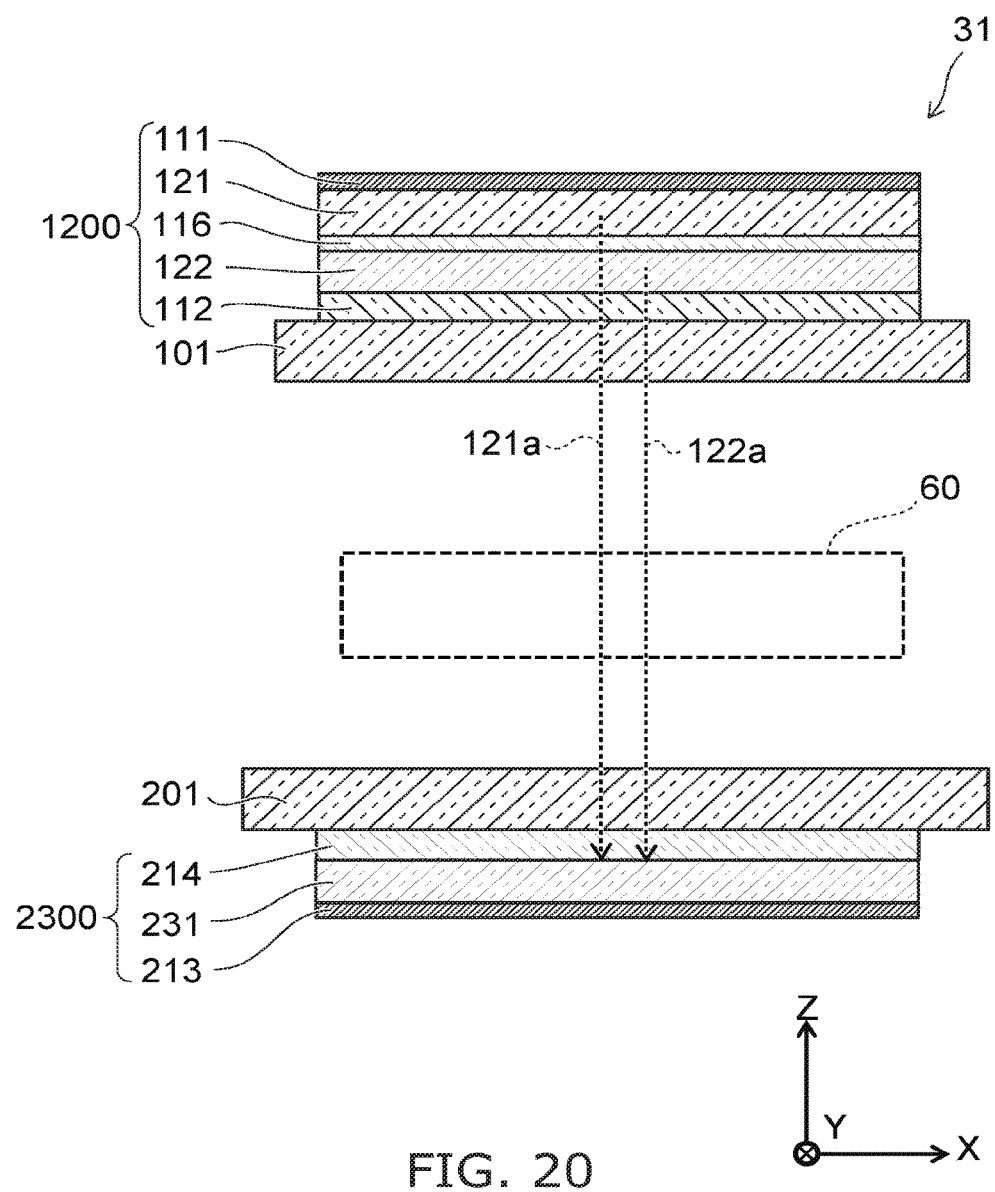
FIG. 20 is a schematic cross-sectional view showing another example of the sensor according to the third embodiment.

FIG. 20 is a schematic cross-sectional view showing another example of the sensor according to the third embodiment. The sensor 31 includes the light emitter 1200 and the light sensor 2300. The light that is radiated from the first light emitting layer 121 and the second light emitting layer 122 passes through the measurement object 60 and is absorbed by the first photoelectric conversion layer 231.

Figure 21B:
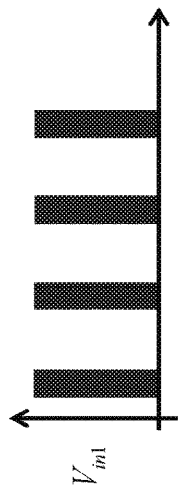
FIG. 21A to FIG. 21D are schematic views showing the method for measuring the blood oxygen concentration using the sensor according to the third embodiment.
Figure 21C:
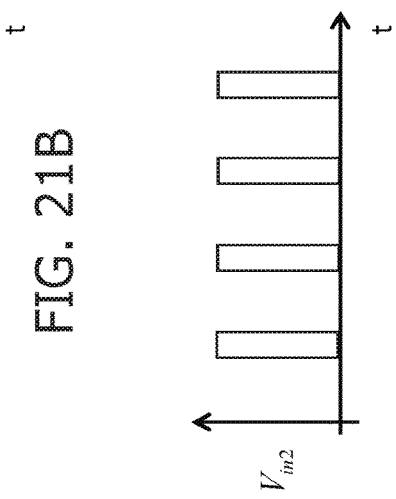
Figure 21D:
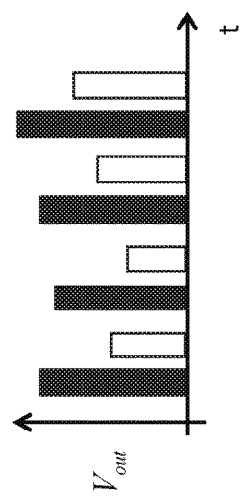

FIG. 21A to FIG. 21D are schematic views showing the method for measuring the blood oxygen concentration using the sensor according to the third embodiment. In FIG. 21B to FIG. 21D, the horizontal axis is the time t. The vertical axis of FIG. 21B is the first input signal $V_{in1}$ input between the first electrode 111 and the sixth electrode 116. The vertical axis of FIG. 21C is the second input signal $V_{in2}$ input between the second electrode 112 and the sixth electrode 116. The vertical axis of FIG. 21D is the output signal $V_{out}$ sensed by the first photoelectric conversion layer 231.

Figure 21A:
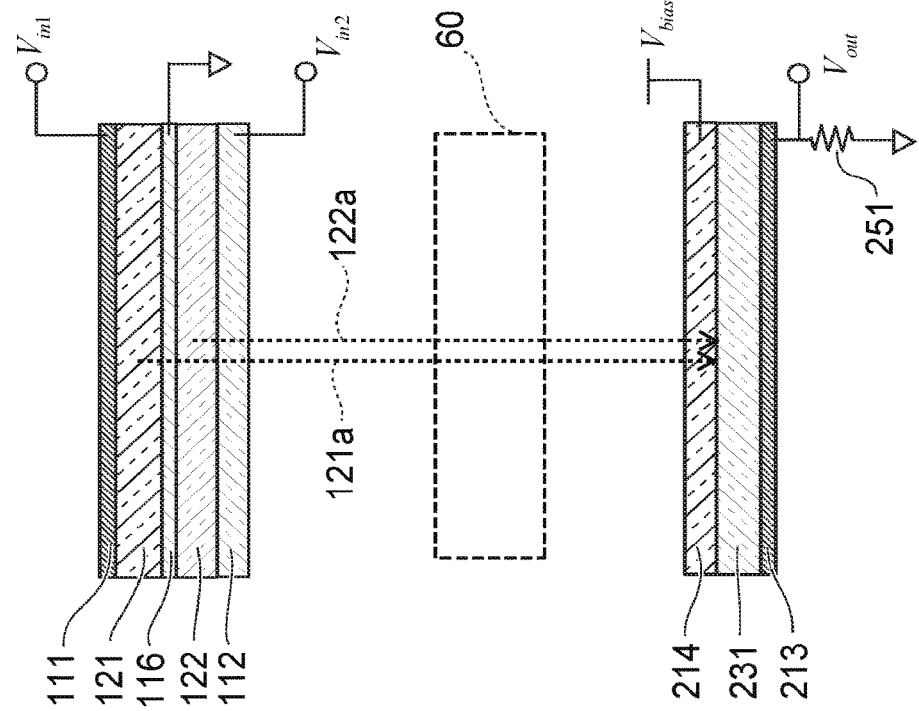

The substrate 101 and the substrate 201 are not shown in FIG. 21A. As shown in FIG. 21B, the first input signal $V_{in1}$ which is, for example, a pulse voltage, is applied between the first electrode 111 and the sixth electrode 116. As shown in FIG. 21C, the second input signal $V_{in2}$ which is, for example, a pulse voltage, is applied between the second electrode 112 and the sixth electrode 116.

The timing at which the pulse voltage of the first input signal $V_{in1}$ is applied is different from the timing at which the pulse voltage of the second input signal $V_{in2}$ is applied. Therefore, the timing at which the light 121a is radiated from the first light emitting layer 121 is different from the timing at which the light 122a is radiated from the second light emitting layer 122.

As a result, as shown in FIG. 21D, the signal based on the light 121a radiated from the first light emitting layer 121 and the signal based on the light 122a radiated from the second light emitting layer 122 appear alternately in the output signal.

Figure 22A:
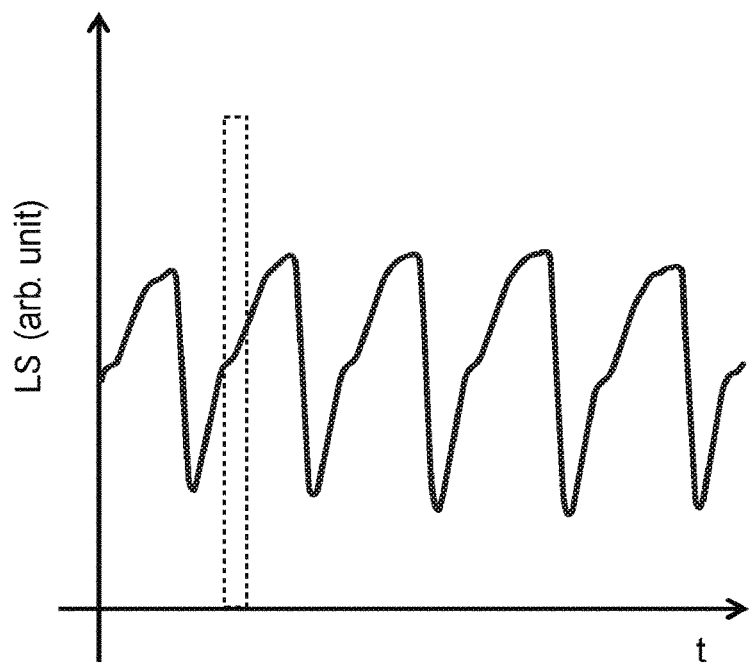
FIG. 22A, FIG. 22B, FIG. 23A, and FIG. 23B are schematic views showing the separated output signals.
Figure 22B:
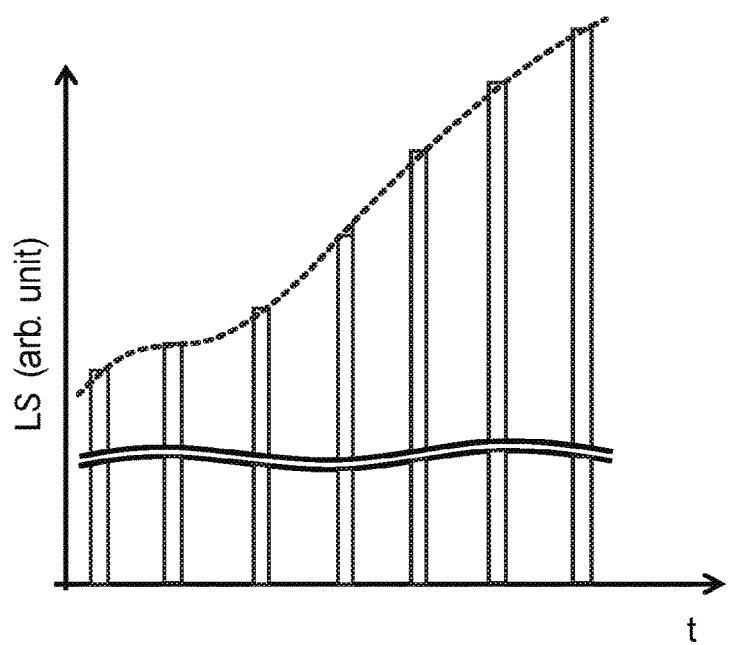
Figure 23A:
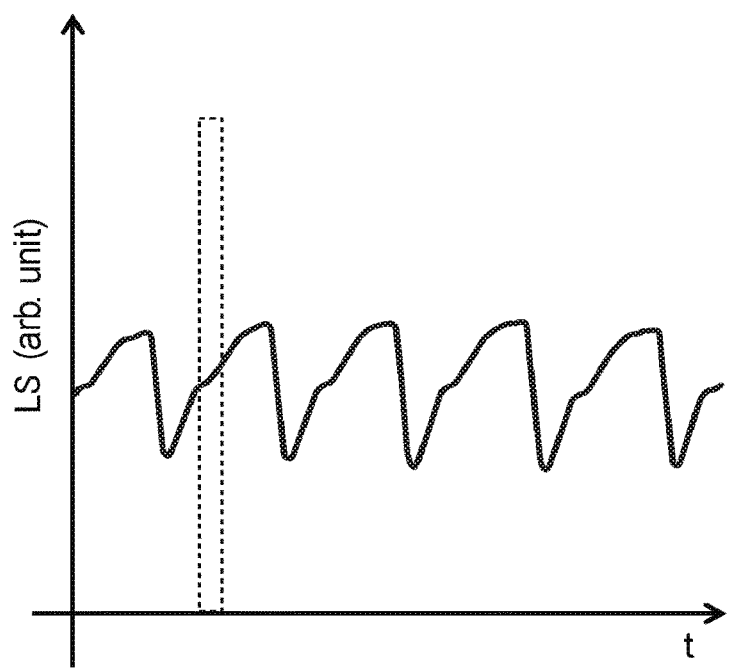
Figure 23B:
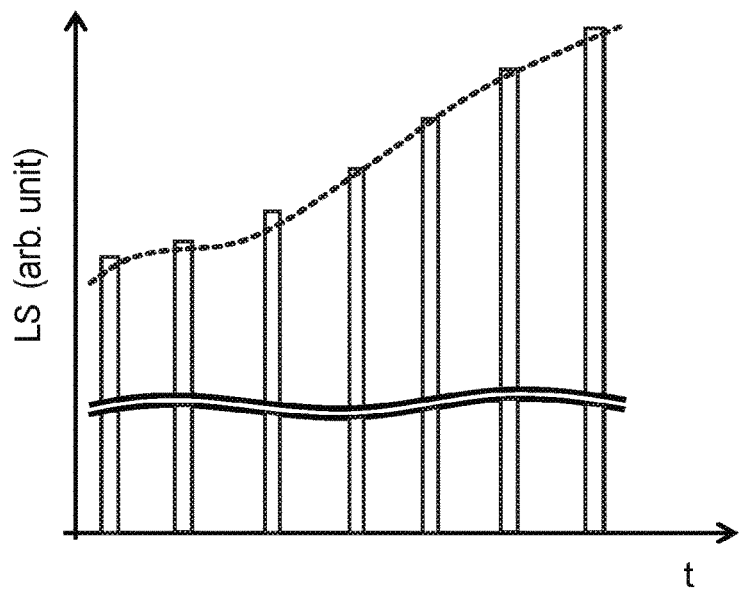

FIG. 22A, FIG. 22B, FIG. 23A, and FIG. 23B are schematic views showing the separated output signals. Specifically, FIG. 22A and FIG. 22B show the state when the signal based on the light 121a is extracted from the output signal shown in FIG. 21D. FIG. 23A and FIG. 23B show the state when the signal based on the light 122a is extracted from the output signal shown in FIG. 21D.

In FIG. 22A, FIG. 22B, FIG. 23A, and FIG. 23B, the horizontal axis is the time t. In FIG. 22A, FIG. 22B, FIG. 23A, and FIG. 23B, the vertical axis is the light intensity LS. The portion surrounded with the broken line in FIG. 22A is enlarged in FIG. 22B. The portion surrounded with the broken line in FIG. 23A is enlarged in FIG. 23B.

In the case where the frequency of the first input signal $V_{in1}$ and the frequency of the second input signal $V_{in2}$ are sufficiently higher than the frequency of the pulse wave, the information relating to the pulse wave is obtained by viewing only the signal of each light pulse. Typically, the pulse wave is about 1 Hz; and the frequency of the pulse voltage can be set to, for example, 100 Hz to 100 KHz. By separating the signal based on the light 121a from the signal based on the light 122a, it is also possible to obtain the blood oxygen concentration using the method described in the first embodiment.

According to the embodiment, a sensor that is more compact is possible. Because the light is radiated from the light emitter 1200 using a pulse voltage, the time that the light emitter 1200 is caused to emit light is short compared to a sensor using a constant voltage. Therefore, the degradation of each light emitting layer included in the light emitter 1200 can be suppressed; and the power consumption can be reduced.

As in the sensor 10 shown in FIG. 2 and FIG. 3, the sensor 30 or 31 may further include the processor 900 in addition to the light emitter and sensor.

FIG. 24A to FIG. 24C are schematic views showing sensors according to the embodiment that are mounted. Each sensor includes, for example, the light emitter 1000, the light sensor 2000, and a controller/signal processor 3000.

In a sensor 40 shown in FIG. 24A, the light emitter 1000 is mounted on a support substrate 1000S. The light sensor 2000 is mounted on a support substrate 2000S that is separated from the support substrate 1000S. The controller/signal processor 3000 is mounted on a support substrate 3000S that is separated from the support substrate 1000S and the support substrate 2000S.

In a sensor 41 shown in FIG. 24B, the light emitter 1000 and the light sensor 2000 are mounted on a common support substrate 1000S. The controller/signal processor 3000 is mounted on a support substrate 3000S that is separated from the support substrate 1000S.

In a sensor 42 shown in FIG. 24C, the light emitter 1000, the light sensor 2000, and the controller/signal processor 3000 are mounted on a common support substrate 1000S.

Other than the configurations shown in FIG. 24A to FIG. 24C, only the light sensor 2000 and the controller/signal processor 3000 may be mounted to a common support substrate. Or, only the light emitter 1000 and the controller/signal processor 3000 may be mounted to a common support substrate.

FIG. 25A to FIG. 25E are schematic views showing applications of the sensor according to the embodiment. In each of the examples, for example, the sensor measures the pulse and/or oxygen concentration of the blood.

In the example shown in FIG. 25A, a sensor 50 is included in a finger ring. For example, the sensor 50 senses the pulse of a finger contacting the sensor 50. In the example shown in FIG. 25B, a sensor 51 is included in an arm band. For example, the sensor 51 senses the pulse of an arm or a foot contacting the sensor 51.

In the example shown in FIG. 25C, a sensor 52 is included in an earphone. In the example shown in FIG. 25D, a sensor 53 is included in eyeglasses. For example, the sensor 52 and the sensor 53 sense the pulse of an ear lobe. In the example shown in FIG. 25E, a sensor 54 is included in a button, a screen, or the like of a mobile telephone or a smartphone. For example, the sensor 54 senses the pulse of a finger contacting the sensor 54.

Figure 26:
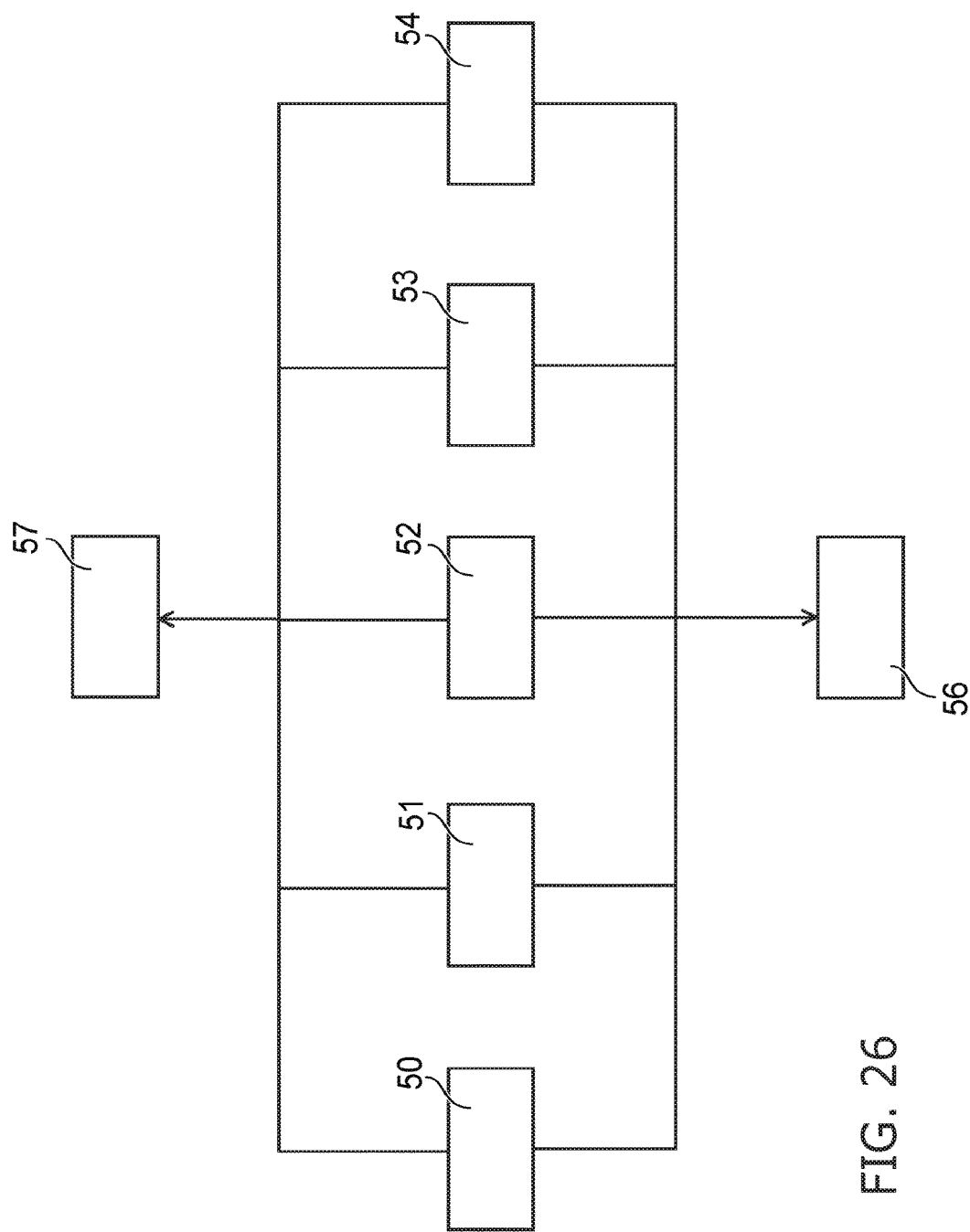
FIG. 26 is a schematic view showing a system using the sensor shown in FIGS. 25A to 25E.

FIG. 26 is a schematic view showing a system using the sensor shown in FIGS. 25A to 25E.

For example, the sensors 50 to 54 transfer the measured data by a wired or wireless method to a device 56 such as a desktop PC, a notebook PC, a tablet terminal, etc. Or, the sensors 50 to 54 may transfer the data to a network 57.

The data that is measured by the sensors can be managed by utilizing the device 56 or the network 57. Or, management or statistical processing may be performed by analyzing the measured data by using an analysis program, etc.

In the case where the measured data is the pulse or oxygen concentration of the blood, the data can be summarized at every arbitrary time interval. For example, the summarized data is utilized for health care. For example, in a hospital, the summarized data is utilized for continuous monitoring of the health condition of a patient.

According to the embodiments recited above, a sensor that can be more compact can be provided.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, embodiments of the invention are described with reference to specific examples. However, the invention is not limited to these specific examples. For example, one skilled in the art may similarly practice the invention by appropriately selecting specific configurations of components included in the first electrode to the eighth electrode, the first light emitting layer, the second light emitting layer, the first photoelectric conversion layer, the second photoelectric conversion layer, the first layer to the sixth layer, the exciton diffusion layer, the controller/signal processor, the recording device, and the display device, etc., from known art; and such practice is within the scope of the invention to the extent that similar effects can be obtained.

Further, any two or more components of the specific examples may be combined within the extent of technical feasibility and are included in the scope of the invention to the extent that the purport of the invention is included.

Moreover, all sensors practicable by an appropriate design modification by one skilled in the art based on the sensors described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
   a light emitter including
   a first electrode,
   a second electrode, the second electrode being light-transmissive, and
   a first light emitting layer provided between the first electrode and the second electrode; and
   a light sensor including
   a third electrode,
   a fourth electrode, the fourth electrode being light-transmissive,
   a fifth electrode provided between the third electrode and the fourth electrode, the fifth electrode being light-transmissive,
   a first photoelectric conversion layer provided between the third electrode and the fifth electrode, and
   a second photoelectric conversion layer provided between the fourth electrode and the fifth electrode, wherein
   the first photoelectric conversion layer includes a third organic substance,
   the second photoelectric conversion layer includes a fourth organic substance,
   a wavelength of light absorbed by the third organic substance is different from a wavelength of light absorbed by the fourth organic substance, and
   a difference between an absorption peak wavelength of the first photoelectric conversion layer and an absorption peak wavelength of the second photoelectric conversion layer is 50 nm or more.

2. The sensor according to claim 1, wherein the first light emitting layer includes a first organic substance.

3. The sensor according to claim 1, wherein
   the light emitter further includes a second light emitting layer provided between the first light emitting layer and the second electrode,
   the first light emitting layer includes a first organic substance,
   the second light emitting layer includes a second organic substance, and
   a peak wavelength of a first light radiated from the first organic substance is different from a peak wavelength of a second light radiated from the second organic substance.

4. The sensor according to claim 3, wherein a difference between the peak wavelength of the first light and the peak wavelength of the second light is 50 nm or more.

5. The sensor according to claim 3, wherein the light emitter further includes a sixth electrode provided between the first light emitting layer and the second light emitting layer, the sixth electrode being light-transmissive.

6. The sensor according to claim 1, wherein a reflectance of the first electrode is higher than a reflectance of the second electrode.

7. The sensor according to claim 1, wherein at least a portion of the light emitter and at least a portion of the light sensor overlap in a first direction, the first direction being from the second electrode toward the first electrode.

8. The sensor according to claim 7, wherein
   the light emitter is provided on a first substrate, the first substrate being light-transmissive,
   the light sensor is provided on a second substrate, the second substrate being light-transmissive, and
   at least a portion of the first substrate and at least a portion of the second substrate are provided between the light emitter and the light sensor.

9. The sensor according to claim 7, wherein
   the light emitter is provided on a first substrate,
   the light sensor is provided on a second substrate, the second substrate being light-transmissive,
   the light emitter is provided between at least a portion of the first substrate and at least a portion of the second substrate, and
   at least a portion of the second substrate is provided between the light emitter and the light sensor.

10. The sensor according to claim 8, wherein at least a portion of the first substrate is provided between the first light emitting layer and the second light emitting layer.

11. The sensor according to claim 8, wherein at least a portion of the second substrate is provided between the first photoelectric conversion layer and the second photoelectric conversion layer.

12. The sensor according to claim 1, wherein at least a portion of the light emitter and at least a portion of the light sensor overlap in a second direction perpendicular to a first direction, the first direction being from the second electrode toward the first electrode.

13. The sensor according to claim 1, further comprising a processor receiving a signal and processing the signal, the signal being sensed by the light sensor.

* * * * *